US012216119B2

(12) United States Patent
Guan

(10) Patent No.: US 12,216,119 B2
(45) Date of Patent: Feb. 4, 2025

(54) IGF-1 ANALYSIS, ADJUSTMENT AND DISEASE MANAGEMENT OF NON-NEUROLOGICAL AND/OR NEUROLOGICAL CONDITIONS

(71) Applicant: THE CGP LAB LIMITED, Rangiora (NZ)

(72) Inventor: Jian Guan, Auckland (NZ)

(73) Assignee: THE CGP LAB LIMITED (NZ)

( * ) Notice: Subject to any disclaimer, the term of this patent is extended or adjusted under 35 U.S.C. 154(b) by 614 days.

(21) Appl. No.: 16/642,863

(22) PCT Filed: Aug. 28, 2018

(86) PCT No.: PCT/NZ2018/050116
§ 371 (c)(1),
(2) Date: Feb. 27, 2020

(87) PCT Pub. No.: WO2019/045575
PCT Pub. Date: Mar. 7, 2019

(65) Prior Publication Data
US 2021/0072240 A1 Mar. 11, 2021

(30) Foreign Application Priority Data

Aug. 28, 2017 (NZ) .......................................... 735002
May 7, 2018 (NZ) .......................................... 742311

(51) Int. Cl.
| G01N 33/569 | (2006.01) |
| A61K 31/352 | (2006.01) |
| A61K 31/7048 | (2006.01) |
| A61K 36/185 | (2006.01) |

(52) U.S. Cl.
CPC ..... *G01N 33/56966* (2013.01); *A61K 31/352* (2013.01); *A61K 31/7048* (2013.01); *A61K 36/185* (2013.01); *G01N 2410/00* (2013.01); *G01N 2800/28* (2013.01)

(58) Field of Classification Search
None
See application file for complete search history.

(56) References Cited

U.S. PATENT DOCUMENTS

| 5,262,162 | A | 11/1993 | Bormann et al. |
| 2003/0109531 | A1 | 6/2003 | Tran |
| 2007/0244039 | A1 | 10/2007 | Tran |
| 2010/0196331 | A1 | 8/2010 | Johnson |
| 2010/0247483 | A1 | 9/2010 | Tran |
| 2015/0257425 | A1 | 9/2015 | Toomey |

FOREIGN PATENT DOCUMENTS

| CN | 105087235 A | 11/2015 |
| EP | 1 607 006 A1 | 12/2005 |
| GB | 1 235 379 | 6/1971 |
| JP | 2010-202597 A | 9/2010 |
| JP | 2017-504808 A | 2/2017 |
| WO | 2003/039487 A2 | 5/2003 |
| WO | WO 2015/013397 A2 | 1/2015 |

OTHER PUBLICATIONS

Guan, et al., "2016 Cyclic Glycine-Proline increased in the cerebrospinal fluid of Parkinson patients after supplementation of blackcurrant anthocyanins: potential biomarker for treatment," 20th International Conference in Movement Disorders; Jun. 18-23, 2016, 2016; Berlin, Germany.
Shukitt-Hale, et al., "Dietary supplementation with fruit polyphenolics ameliorates age-related deficits in behavior and neuronal markers of inflammation and oxidative stress," Age, vol. 27, 2005, pp. 49-57.
Castro-Acosta, et al., "Drinks containing anthocyanin-rich blackcurrant extract decrease postprandial blood glucose, insulin and incretin concentrations," Journal of Nutritional Biochemistry, vol. 38, 2016, pp. 154-161.
Singh-Mallar, et al., "Maternally Administered Cyclic Glycine-Proline Increases Insulin-Like Growth Factor-I Bioavailability and Novelty Recognition in Developing Offspring," Endocrinology, vol. 157(8), Aug. 2016, pp. 3130-3139.
Dong, Xiang, et al. "The relationship between serum insulin-like growth factor I levels and ischemic stroke risk." *PloS one* 9.4 (2014): e94845.
Guan, Jian, et al. "The role for IGF-1-derived small neuropeptides as a therapeutic target for neurological disorders." *Expert opinion on therapeutic targets* 19.6 (2015): 785-793.
International Search Report and Written Opinion dated Nov. 26, 2018, for International Application No. PCT/NZ2018/050116, 11 pages.

*Primary Examiner* — Michael V Meller
(74) *Attorney, Agent, or Firm* — FROST BROWN TODD LLP

(57) ABSTRACT

Described herein are improvements relating to IGF-1 analysis, adjustment and disease management of non-neurological and/or neurological conditions. More specifically, methods relating to the clinical application of cyclic glycine-proline (cGP) biomarker for prediction of risk and recovery of non-neurological and/or neurological conditions with IGF-1 dysfunction and the use of a cGP containing organic or plant based material such as concentrated extract of blackcurrant anthocyanins (BCA) for the treatment of same. The methods more accurately measure IGF-1 function in vivo indirectly using cGP and cGP/IGF-1 ratio along with a means to adjust cGP and cGP/IGF-1 ratio (and hence active IGF-1 concentration), and specific treatment methods for individuals with a lower or reduction of cGP level relative to a standard set of baseline data.

3 Claims, 12 Drawing Sheets

IGF-1 ANALYSIS, ADJUSTMENT AND DISEASE MANAGEMENT OF NON-NEUROLOGICAL AND/OR NEUROLOGICAL CONDITIONS

CROSS-REFERENCE TO RELATED APPLICATION(S)

This application is a National Phase Patent Application and claims priority to and the benefit of International Application Number PCT/NZ2018/050116, filed on Aug. 28, 2018, which claims priority to New Zealand Patent Application Number 735002, filed on Aug. 28, 2017, and New Zealand Patent Application Number 742311, filed on May 7, 2018, the entire contents of all of which are incorporated herein by reference.

TECHNICAL FIELD

Described herein are improvements relating to IGF-1 analysis, adjustment and disease management of non-neurological and/or neurological conditions. More specifically, methods relating to the clinical application of cyclic glycine-proline (cGP) biomarker for prediction of risk and recovery of non-neurological and/or neurological conditions with IGF-1 dysfunction and the use of a cGP containing organic or plant based material such as concentrated extract of blackcurrant anthocyanins (BCA) for the treatment of same.

BACKGROUND ART

Insulin-like growth factor-1 (IGF-1) is a protein produced as an endocrine hormone. It is a primary mediator of the effects of growth hormone and stimulates body growth in nearly every cell in the body. In addition to growth effects, IGF-1 can also regulate nerve cells as well as cellular DNA synthesis.

It is also a neurotropic factor and plays a critical role in a variety of neuronal functions such as cognitive function. IGF-1 is produced throughout life, but is lowest in infants (particularly the neonates), increases during adulthood, and declines with age. Measuring IGF-1 function may be a biomarker of cognitive decline with age and in turn be used to aid in knowing whether interventions such as drug treatments may be useful or not and when to commence such treatments.

Plasma IGF-1 concentration however has historically been a poor biomarker for IGF-1 function as direct measurement of IGF-1 provides inconsistent results that cannot be used with any degree of confidence. Historical use for example may be to test for IGF-1 in blood as a screening test for growth hormone deficiency and unusual growth patterns but the results are primarily a guide of total IGF-1 and not a specific measure of active IGF-1.

It is understood that inconsistent results from direct IGF-1 measurement may be due to the majority of IGF-1 in vivo being inactive. It is the active portion that is key. In plasma, more than 95% of IGF-1 binds to IGF-binding protein-3 (IGFBP-3) and once bound, the IGF-binding protein-3 prevents activation of the IGF-1 functional receptor. Therefore, when IGF-1 is measured directly, there is no distinction between active and inactive form, and hence no knowledge of the true active amount of IGF-1 in vivo, the active portion being the biomarker of concern.

The ratio of IGF-1/IGFBP-3 may be used as an alternative for indicating unbound, bioactive IGF-1, but in practice, this ratio does not provide clear indications either as the majority of IGFBP-3 does not bind to IGF-1.

As may be appreciated, an alternative measure of IGF-1 may be beneficial as a means to track IGF-1 function and hence use this measure as a biomarker of patient health. For example, cyclic glycine-proline (cGP), a metabolite of IGF-1 is neuroprotective through improving/normalising bioavailability of IGF-1 in plasma.

Corresponding to understanding IGF-1 levels may be the desire to then adjust or support a patient's natural immune and repair system by increasing their IGF-1 active portion.

Further, since IGF-1 is intimately linked to a variety of animal functions, one of many being neurodegenerative function, ways to both measure associated changes and treat, ameliorate or accelerate healing in various related conditions may be of use.

The human body has the ability to protect itself from injury and illness, for example our hormone system becomes more active. However, the capability to help us recover is not always effective in order to achieve a full recovery, especially in older people due to the loss of hormones with age. Stroke happens to young and aged populations. While younger stroke patients can make a more rapid and better recovery, the recovery from older patients can be slow and poor. IGF-1 function is also important for stroke recovery. Thus, a reliable biomarker for IGF-1 function in stroke may be used for the prognosis of a stroke or other neurological conditions and even a method of predicting the ability of stroke recovery may help to design clinical managements for individual patients. However, as above plasma IGF-1 or IGF-1/IGF binding protein-3 (IGFBP-3) ratio is not reliable biomarker. Thus, it would be useful to find a potential biomarker for IGF-1 function to assist with spontaneous recovery of stroke patients and method of treatment of same.

As an age related condition Parkinson's disease (PD) is the second most common neurodegenerative condition. Insulin-like growth factor-1 (IGF-1) is a neurotrophic factor and plays an essential role in neuronal survival and maintaining brain function. IGF-1 resistance, characterized by an increase in circulating IGF-1 and impairment of IGF-1 function, has been reported to be associated with neurological deficits and cognitive decline in PD patients. As noted above, changes in IGF-1 concentration in serum have been used as a biomarker for IGF-1 dysfunction used for monitoring the prognosis and treatment response in PD, though this is still debatable. High consumption of berry-fruits has been reported to be associated with a lower risk of PD, although the mechanism underlying this putative benefit remains unknown.

Further aspects and advantages of the improvements relating to the analysis of IGF-1 function, adjustment and disease management of non-neurological and/or neurological conditions due to IGF-1 dysfunction will become apparent from the ensuing description that is given by way of example only.

SUMMARY

Described herein are methods relating to the clinical application of cyclic glycine-proline (cGP) biomarker for prediction of risk and recovery of non-neurological and/or neurological conditions with IGF-1 dysfunction and the use of cGP containing organic or plant based material such as a concentrated extract of blackcurrant anthocyanins (BCA) for the treatment of same. The methods more accurately measure IGF-1 function in vivo indirectly using cGP and cGP/IGF-1 ratio along with a means to adjust cGP and cGP/IGF-1 ratio (and hence active IGF-1 concentration), and specific treatment methods for individuals with a lower or reduction of cGP level relative to a standard set of baseline data.

In a first aspect, there is provided a method of treating non-neurological and/or neurological conditions associated with IGF-1 dysfunction in an animal comprising the steps of:
  a) obtaining a biological specimen from the animal;
  b) measuring a concentration of cyclic glycine-proline (cGP) as a biomarker for active concentration dependent insulin-like growth factor 1 (IGF-1) bioavailability in the biological specimen;
  c) comparing either the measured cGP concentration and/or ratio of cGP concentration to total measured amount of IGF-1 in the biological specimen to a standard to confirm whether or not, in a continuum of results, the measured cGP concentration and/or ratio of cGP concentration to total measured amount of IGF-1 conforms to the relative standard for estimating IGF-1 function of the individual; and
  d) administering a therapeutically effective amount of a concentrated extract of blackcurrant anthocyanins (BCA) to the animal to:
prevent a decrease in concentration of cGP and/or cGP to total measured IGF-1 ratio in an animal; and/or
maintain a pre-existing concentration of cGP and/or cGP to total measured IGF-1 ratio in an animal; and/or
increase the concentration of cGP and/or cGP to total measured IGF-1 ratio in an animal.

In a second aspect, there is provided a method of predicting a risk of a non-neurological and/or neurological condition with age in an animal utilising cyclic glycine-proline (cGP) as a biomarker with altered IGF-1 function comprising the steps of:
  a) obtaining a biological specimen from the animal;
  b) measuring a concentration of cyclic glycine-proline (cGP) as a biomarker for active concentration dependent insulin-like growth factor 1 (IGF-1) bioavailability in the biological specimen at a first set age of the animal, or an initial stage of the neurological condition, or before treatment of an therapeutically effective amount of a concentrated extract of blackcurrant anthocyanins (BCA) to the animal;
  c) re-measuring the concentration of cyclic glycine-proline (cGP) biomarker for active concentration dependent insulin-like growth factor 1 (IGF-1) bioavailability in the biological specimen at further set age intervals of the animal or further stage of the non-neurological and/or neurological condition, or after treatment of the therapeutically effective amount of the concentrated extract of blackcurrant anthocyanins (BCA) to the animal;
  d) comparing either the measured cGP concentration and/or ratio of cGP concentration to total measured amount of IGF-1 in the biological specimen at the set age intervals relative to the first set age, or the initial stage of the non-neurological and/or neurological condition with IGF-1 dysfunction, or before the treatment of the therapeutically effective amount of a concentrated extract of blackcurrant anthocyanins (BCA) to the animal, in a continuum of results, to confirm whether or not there is a change in the measured cGP concentration and/or ratio of cGP concentration to total measured amount of IGF-1 thereby determining whether the animal is at an increased risk of developing a non-neurological and/or neurological condition from cognitive decline relative to a standard set of baseline data, and wherein the above measured ratio is used to select individual patients for BCA treatment and a suitable dosage for the BCA treatment therein.

In a third aspect, there is provided a method of predicting the spontaneous recovery of an animal with a non-neurological and/or neurological conditions with IGF-1 dysfunction utilising cyclic glycine-proline (cGP) as a biomarker for IGF-1 function comprising the steps of:
  a) obtaining a biological specimen from the animal;
  b) measuring a concentration of cyclic glycine-proline (cGP) biomarker and active concentration dependent insulin-like growth factor 1 (IGF-1) bioavailability in the biological specimen at a baseline of the animal from onset of the non-neurological and/or neurological condition (<72 h); and
  c) re-measuring the concentration of cyclic glycine-proline (cGP) biomarker and active concentration dependent insulin-like growth factor 1 (IGF-1) bioavailability in the biological specimen at further regular intervals of the animal during recovery,
  d) evaluating functional recovery of the animal from the baseline and at further set intervals, and
wherein the baseline concentration of CGP from a continuum of data predicts the short term outcome of non-neurological and/or neurological condition recovery of the animal such that a greater baseline cGP concentration, the more positive prognosis for the animal based on the evaluation of functional recovery.

In a fourth aspect, there is provided the use of a concentrated extract of blackcurrant anthocyanins (BCA) in the manufacture of a medicament formulated to:
  prevent a decrease in concentration of cGP and/or cGP to total measured IGF-1 ratio in an animal; and/or
  maintain a pre-existing concentration of cGP and/or cGP to total measured IGF-1 ratio in an animal; and/or
  increase the concentration of cGP and/or cGP to total measured IGF-1 ratio in an animal.

In a fifth aspect, there is provided the use of a concentrated extract of blackcurrant anthocyanins (BCA) in the manufacture of a medicament formulated for oral administration to ameliorate the effects of and/or treat non-neurological and/or neurological conditions in a patient in need thereof.

In a sixth aspect, there is provided an extract comprising a therapeutically effective amount of concentrated blackcurrant anthocyanin (BCA) formulated for administration to an animal to:
  prevent a decrease in concentration of cGP and/or cGP to total measured IGF-1 ratio in an animal; and/or
  maintain a pre-existing (normal/physiological) concentration of cGP and/or cGP to total measured IGF-1 ratio in an animal; and/or
  increase or to normalise the concentration of cGP and/or cGP to total measured IGF-1 ratio in an animal.

In a seventh aspect, there is provided a method for ameliorating the effects of hypertension and/or a stroke; and/or treating hypertension and/or stroke; and/or reducing the symptoms associated with hypertension and/or stroke in a patient in need thereof, wherein the method comprises administering a therapeutically effective amount of a concentrated extract of blackcurrant anthocyanins (BCA).

In an eighth aspect, there is provided a method for ameliorating the effects of and/or treating Parkinson's disease or the symptoms associated with Parkinson's disease, or complications associated with cognitive impairment in a patient in need thereof, wherein the method comprises administering a therapeutically effective amount of a concentrated extract of blackcurrant anthocyanins (BCA).

In a ninth aspect, there is provided a method of treating non-neurological and/or neurological conditions associated with IGF-1 dysfunction in an animal comprising the steps of:
a) obtaining a biological specimen from the animal;
b) measuring a concentration of cyclic glycine-proline (cGP) biomarker for active concentration dependent insulin-like growth factor 1 (IGF-1) bioavailability in the biological specimen;
c) comparing either the measured cGP concentration and/or ratio of cGP concentration to total measured amount of IGF-1 in the biological specimen to a standard to confirm whether or not, in a continuum of results, the measured cGP concentration and/or ratio of cGP concentration to total measured amount of IGF-1 conforms to the relative standard for estimating IGF-1 function of the individual; and
d) administering a therapeutically effective amount of a concentrated extract of a cGP containing organic or plant based material to the animal to:
prevent a decrease in concentration of cGP and/or cGP to total measured IGF-1 ratio in an animal; and/or
maintain a pre-existing concentration of cGP and/or cGP to total measured IGF-1 ratio in an animal; and/or
increase the concentration of cGP and/or cGP to total measured IGF-1 ratio in an animal.

In a tenth aspect, there is provided a method of predicting a risk of a non-neurological and/or neurological condition with age in an animal utilising cyclic glycine-proline (cGP) as a biomarker with altered IGF-1 function comprising the steps of:
a) obtaining a biological specimen from the animal;
b) measuring a concentration of cyclic glycine-proline (cGP) biomarker for active concentration dependent insulin-like growth factor 1 (IGF-1) bioavailability in the biological specimen at a first set age of the animal, or an initial stage of the non-neurological and/or neurological condition, or before treatment of an therapeutically effective amount of a concentrated extract of cGP containing organic or plant based material to the animal;
c) re-measuring the concentration of cyclic glycine-proline (cGP) biomarker for active concentration dependent insulin-like growth factor 1 (IGF-1) bioavailability in the biological specimen at further set age intervals of the animal or further stage of the non-neurological and/or neurological condition, or after treatment of the therapeutically effective amount of the concentrated extract of cGP containing organic or plant based material;
d) comparing either the measured cGP concentration and/or ratio of cGP concentration to total measured amount of IGF-1 in the biological specimen at the set age intervals relative to the first set age, or the initial stage of the non-neurological and/or neurological condition, or before the treatment of the therapeutically effective amount of a concentrated extract of cGP containing organic or plant based material to the animal, in a continuum of results, to confirm whether or not there is a change in the measured cGP concentration and/or ratio of cGP concentration to total measured amount of IGF-1 thereby determining whether the animal is at an increased risk of developing a non-neurological and/or neurological condition from cognitive decline relative to a standard set of baseline data, and wherein the above measured ratio is used to select individual patients for cGP containing organic or plant based material treatment and a suitable dosage for the cGP containing organic or plant based material treatment therein.

In an eleventh aspect, there is provided the use of a concentrated extract of a cGP containing organic or plant based material in the manufacture of a medicament formulated to:
prevent a decrease in concentration of cGP and/or cGP to total measured IGF-1 ratio in an animal; and/or
maintain a pre-existing concentration of cGP and/or cGP to total measured IGF-1 ratio in an animal; and/or
increase the concentration of cGP and/or cGP to total measured IGF-1 ratio in an animal.

In a twelfth aspect, there is provided the use of a concentrated extract of cGP containing organic or plant based material in the manufacture of a medicament formulated for oral administration to ameliorate the effects of and/or treat non-neurological and/or neurological conditions in a patient in need thereof.

In a thirteenth aspect, there is provided an extract comprising a therapeutically effective amount of concentrated extract of cGP containing organic or plant based material formulated for administration to an animal to:
prevent a decrease in concentration of cGP and/or cGP to total measured IGF-1 ratio in an animal; and/or
maintain a pre-existing (normal/physiological) concentration of cGP and/or cGP to total measured IGF-1 ratio in an animal; and/or
increase or to normalise the concentration of cGP and/or cGP to total measured IGF-1 ratio in an animal.

In a fourteenth aspect, there is provided a method for ameliorating the effects of hypertension and/or a stroke; and/or treating hypertension and/or stroke; and/or reducing the symptoms associated with hypertension and/or stroke in a patient in need thereof, wherein the method comprises administering a therapeutically effective amount of a concentrated extract of cGP containing organic or plant based material.

In a fifteenth aspect, there is provided a method for ameliorating the effects of and/or treating Parkinson's disease or the symptoms associated with Parkinson's disease, or complications associated with cognitive impairment in a patient in need thereof, wherein the method comprises administering a therapeutically effective amount of a concentrated extract of cGP containing organic or plant based material.

Advantages of the above may be varied. With respect to a biomarker, cGP as noted is a stable metabolite of IGF-1 and based on the inventor's work, is easily measured in biological specimens taken from an animal. cGP does not have the same variability as IGF-1 in terms of distinguishing active from inactive forms and hence is more reliable than measuring total IGF-1. With respect to the described methods of measuring the changes in cGP and/or addressing neurological conditions, an advantage of the clinical application of cyclic glycine-proline (cGP) as a reliable biomarker allows for selection of suitable patients for treatment and individual dosage regimes. The increase of cGP indicates the risk of a neurological condition and the reduction of cGP indicates the stage of the neurological condition. Advantageously, suitable patients for treatment may be selected based on their cGP level and the changes of cGP levels can be easily monitored for a tailored or personalised treatment dosage regime.

Adjusting the dosage regime of BCA and/or extract of cGP containing organic or plant based material allows for effective treatment of the non-neurological and/or neurological conditions, thus improving long-term recovery (beyond 3 months) and prevention of long time complications (cognitive impairment) associated with non-neurological and/or neurological conditions. A further advantage is that cGP levels can simply be monitored by measuring urine samples for ease of analysis and critical for large scale clinical trials of BCA/cGP containing organic plant extracts in the future.

The use of blackcurrant in such a measurable and known manner has not been known or completed in the art. Blackcurrant juice or other forms of blackcurrant (not the extracts noted) have not been used in the known and measurable manner now possible and as described herein. The stroke and Parkinson's findings in particular exhibit a new or at least alternative use for blackcurrant that may provide significant and measurable benefit to patients potentially also without interfering with existing art treatments or causing unwanted side effects. Further, with respect to natural products and associated bioactive compounds generally, the methods and uses described herein provide unique ways to know when it is appropriate to intervene with a treatment and further, provide ways to measure the success or otherwise of a treatment. This insight into timing and efficacy is something many pharmaceutical drugs would aspire to and not something commonly observed in natural products containing bioactive compounds.

BRIEF DESCRIPTION OF THE DRAWINGS

Further aspects of the methods relating to the clinical application of cyclic glycine-proline (cGP) biomarker for prediction of risk and the recovery of non-neurological and neurological conditions associated with IGF-1 dysfunction and the use of a cGP containing organic or plant based material such as a concentrated extract of blackcurrant anthocyanins (BCA) for the treatment of same will become apparent from the following description that is given by way of example only and with reference to the accompanying drawings in which.

and c-GP/IGF-1 ratio (FIG. 15D) between normal control (no stroke) and base-line level of stroke patients <3d.

DETAILED DESCRIPTION

Figure 1:
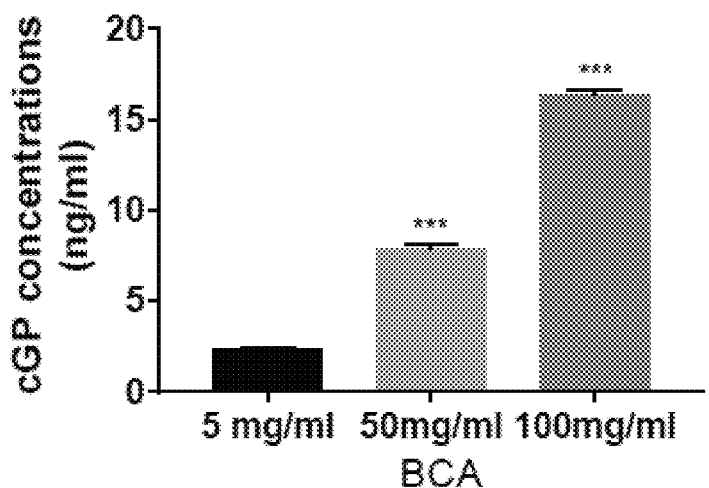
FIG. 1 shows a dose dependent increase of cGP in the BCA. Data presented as mean±SEM, $p<0.0001$.

As noted above, described herein are methods relating to the clinical application of cyclic glycine-proline (cGP) biomarker for prediction of risk and recovery of non-neurological and neurological conditions and the use of a cGP containing organic or plant based material such as a concentrated extract of blackcurrant anthocyanins (BCA) for the treatment of same. The methods more accurately measure IGF-1 in vivo indirectly using cGP and cGP/IGF-1BP3 ratio along with a means to adjust cGP and cGP/IGF-1 ratio (and hence active IGF-1 concentration), and specific treatment methods for individuals with a lower or reduction of cGP level relative to a standard set of baseline data.

For the purposes of this specification, the term 'about' or 'approximately' and grammatical variations thereof mean a quantity, level, degree, value, number, frequency, percentage, dimension, size, amount, weight or length that varies by as much as 30, 25, 20, 15, 10, 9, 8, 7, 6, 5, 4, 3, 2, or 1% to a reference quantity, level, degree, value, number, frequency, percentage, dimension, size, amount, weight or length.

The term 'substantially' or grammatical variations thereof refers to at least about 50%, for example 75%, 85%, 95% or 98%.

The term 'comprise' and grammatical variations thereof shall have an inclusive meaning—i.e. that it will be taken to mean an inclusion of not only the listed components it directly references, but also other non-specified components or elements.

The term blackcurrant anthocyanins (BCA) should be understood to be an extract of blackcurrant and throughout the specification and claims, BCA may be interchangeably replaced with a blackcurrant concentrate and/or single strength juice. Furthermore, the BCA extract and/or concentrate may be a source or carrier of cGP irrespective of whether anthocyanins are present.

In a first aspect, there is provided a method of treating non-neurological and/or neurological conditions in an animal comprising the steps of:
  a) obtaining a biological specimen from the animal;
  b) measuring a concentration of cyclic glycine-proline (cGP) biomarker for active concentration dependent insulin-like growth factor 1 (IGF-1) bioavailability in the biological specimen;
  c) comparing either the measured cGP concentration and/or ratio of cGP concentration to total measured amount of IGF-1 in the biological specimen to a standard to confirm whether or not, in a continuum of results, the measured cGP concentration and/or ratio of cGP concentration to total measured amount of IGF-1 conforms to the relative standard for estimating IGF-1 function of the individual; and
  d) administering a therapeutically effective amount of a concentrated extract of blackcurrant anthocyanins (BCA) to the animal to:
prevent a decrease in concentration of cGP and/or cGP to total measured IGF-1 ratio in an animal; and/or
maintain a pre-existing concentration of cGP and/or cGP to total measured IGF-1 ratio in an animal; and/or
increase the concentration of cGP and/or cGP to total measured IGF-1 ratio in an animal.

In a second aspect, there is provided a method of predicting a risk of a non-neurological and/or neurological condition with age in an animal utilising cyclic glycine-proline (cGP) as a biomarker with altered IGF-1 function comprising the steps of:
  a) obtaining a biological specimen from the animal;
  b) measuring a concentration of cyclic glycine-proline (cGP) biomarker for active concentration dependent insulin-like growth factor 1 (IGF-1) bioavailability in the biological specimen at a first set age of the animal, or an initial stage of the neurological condition, or before treatment of an therapeutically effective amount of a concentrated extract of blackcurrant anthocyanins (BCA) to the animal;
  c) re-measuring the concentration of cyclic glycine-proline (cGP) biomarker for active concentration dependent insulin-like growth factor 1 (IGF-1) bioavailability in the biological specimen at further set age intervals of the animal or further stage of the non-neurological and/or neurological condition, or after treatment of the therapeutically effective amount of the concentrated extract of blackcurrant anthocyanins (BCA) to the animal;
  d) comparing either the measured cGP concentration and/or ratio of cGP concentration to total measured amount of IGF-1 in the biological specimen at the set age intervals relative to the first set age, or the initial stage of the neurological condition, or before the treatment of the therapeutically effective amount of a concentrated extract of blackcurrant anthocyanins (BCA) to the animal, in a continuum of results, to confirm whether or not there is a change in the measured cGP concentration and/or ratio of cGP concentration to total measured amount of IGF-1 thereby determining whether the animal is at an increased risk of developing a non-neurological and/or neurological condition from cognitive decline relative to a standard set of baseline data, and wherein the above measured ratio is used to select individual patients for BCA treatment and a suitable dosage for the BCA treatment therein.

In a third aspect, there is provided a method of predicting the spontaneous recovery of an animal with a non-neurological and/or neurological condition utilising cyclic glycine-proline (cGP) as a biomarker for IGF-1 function comprising the steps of:
  a) obtaining a biological specimen from the animal;
  b) measuring a concentration of cyclic glycine-proline (cGP) biomarker and active concentration dependent insulin-like growth factor 1 (IGF-1) bioavailability in the biological specimen at a baseline of the animal from onset of the non-neurological and/or neurological condition (<48 h); and
  c) re-measuring the concentration of cyclic glycine-proline (cGP) biomarker and active concentration dependent insulin-like growth factor 1 (IGF-1) bioavailability in the biological specimen at further regular intervals of the animal during recovery,
  d) evaluating functional recovery of the animal from the baseline and at further set intervals, and
wherein the baseline concentration of CGP from a continuum of data predicts the short term outcome of neurological condition recovery of the animal such that a greater baseline cGP concentration, the more positive prognosis for the animal based on the evaluation of functional recovery.

Cyclic glycine-proline (cGP) is a stable fragment naturally formed by unbound and bioactive IGF-1. cGP competes with IGF-1 inactivation to the bound form of IGFBP-3 in a concentration dependent manner. The inventor has found that cGP is a measurable and reliable biomarker correlated strongly to the amount of active IGF-1 as a result of the concentration dependent manner of inactivation noted above. That is, by measuring cGP concentration, the presence or otherwise of active IGF-1 function can be measured instead of reliance on variable direct IGF-1 measured results.

The inventor's work has shown that a higher concentration of cGP would free more IGF-1 from IGFBP-3 via the concentration dependent manner noted above hence, leading to an increase in bioavailable IGF-1.

In addition to direct cGP measurement, the inventors have also identified that relative concentrations of cGP to IGF-1 (i.e. the cGP/IGF-1 ratio) may also represent the amount of bioavailable IGF-1 in a patient, thus may also potentially fulfil the role for a suitable biomarker for IGF-1 associated cognitive function. It also has been found that the increase in cGP indicates the risk of a neurological condition and the reduction of cGP correlates to the stage of the neurological condition. Hence, it is envisaged that that the treatment with BCA may prevent or delay the on-set of cognitive decline.

The term 'biomarker' as used herein refers to cGP or the ratio of cGP to total IGF-1 traceable in an animal as a means to examine a function of animal health and function. Health and function may comprise but are not limited to detection of a 'normal' or 'healthy' state for the animal relative to either a historical standard measurement for the animal or for a population. Health and function may also comprise detection of a non-normal or unhealthy animal state perhaps linked with a condition, disease or unusual state. As may be appreciated, terms such as 'normal' and 'healthy' are subjective terms, however in the context of this specification, the terms are a relative measure of the biomarker compound or ratio noted compared to either historical details about the animal and/or variation to a population referred to as a standard.

As noted above, the standard may be based on a set of data collected for an individual animal. For example, for a period of time—say 1 week to 6 months to 2 years—averaged cGP and cGP to total IGF-1 ratio data may be collected for the animal. Variations in the biomarker concentration or ratio may be observed and analysed to find a 'typical' figure for the animal and that data and the extent of any deviations used to understand a normal or standard figure versus a typical variation and hence confirm when a non-normal or atypical change occurs.

The standard may instead, or in conjunction with individual animal data, be based on a set of data collected for a population. The population may for example be a gender group, a group defined by age, a group defined by symptom, condition or disease state and so on.

The cGP and/or IGF-1 may be measured in a biological specimen taken from the animal. For the purposes of this specification, the terms 'biological specimen', 'bodily sample', or 'sample' may be used interchangeably and refer collectively to a specimen taken or extracted from a patient, stored and later analysed. Techniques for extraction of the specimen may for example be via swabs, venipuncture, sticks, biopsy, fractionation, urination, stool sample and so on. In selected embodiments, the biological specimen may be: cerebrospinal fluid (CSF), plasma, urine, any other biological specimens (tears and any other bodily function) and combinations thereof.

cGP and/or total IGF-1 in the biological specimen may be measured by techniques selected from: ELISA, HPLC, mass spectrometry, and combinations thereof. Other art analysis techniques may also be used and reference to these techniques should not be seen as limiting.

In a fourth aspect, there is provided the use of a concentrated extract of blackcurrant anthocyanins (BCA) in the manufacture of a medicament formulated to:
  prevent a decrease in concentration of cGP and/or cGP to total measured IGF-1 ratio in an animal; and/or
  maintain a pre-existing concentration of cGP and/or cGP to total measured IGF-1 ratio in an animal; and/or
  increase the concentration of cGP and/or cGP to total measured IGF-1 ratio in an animal.

In a fifth aspect, there is provided the use of a concentrated extract of blackcurrant anthocyanins (BCA) in the manufacture of a medicament formulated for oral administration to ameliorate the effects of and/or treat non-neurological and/or neurological conditions in a patient in need thereof.

In a sixth aspect, there is provided an extract comprising a therapeutically effective amount of concentrated blackcurrant anthocyanin (BCA) formulated for administration to an animal to:
  prevent a decrease in concentration of cGP and/or cGP to total measured IGF-1 ratio in an animal; and/or
  maintain a pre-existing (normal/physiological) concentration of cGP and/or cGP to total measured IGF-1 ratio in an animal; and/or
  increase or to normalise the concentration of cGP and/or cGP to total measured IGF-1 ratio in an animal.

In a seventh aspect, there is provided a method for ameliorating the effects of hypertension and/or a stroke; and/or treating hypertension and/or stroke; and/or reducing the symptoms associated with hypertension and/or stroke in a patient in need thereof, wherein the method comprises administering a therapeutically effective amount of a concentrated extract of blackcurrant anthocyanins (BCA).

The inventor has found that when applying BCA to a patient with hypertension (high blood pressure), their blood pressure reduces to acceptable base levels.

The non-neurological conditions or diseases for treatment and to predict recovery may be selected from, but not limited to hypertension, acute brain injuries (for example, concussion), weight changes in obese women and post-natal development.

In an eighth aspect, there is provided a method of ameliorating the effects of and/or treating Parkinson's disease or the symptoms associated with Parkinson's disease, or complications associated with cognitive impairment in a patient in need thereof, wherein the method comprises administering a therapeutically effective amount of a concentrated extract of blackcurrant anthocyanins (BCA).

The neurological conditions or diseases for treatment may be selected from, but not limited to Cerebrovascular accident (CVA) or stroke, Mild Cognitive Impairment (MCI), Alzheimer's, vascular dementia, hypertension and its associated brain complications, Parkinson's and/or any other ageing related conditions or IGF-1 deficiency related conditions.

Stroke is an exemplary neurological condition in which poor blood flow to the brain results in cell death typically resulting in part of the brain not working properly. The inventor has identified via the biomarker noted above that cGP concentration and cGP to total IGF-1 ratio changes in stroke patients and the extent to which the cGP or ratio decreases is a strong indicator of patient recovery and outcomes. Lower decreases are associated with faster recovery and potentially fewer on-going issues. The exact mechanism for this is not proven however, since IGF-1 is associated with growth it follows that a lower cGP level or cGP to total IGF-1 ratio corresponds to less active IGF-1 and hence slower growth of neural pathways hence a slower recovery. Based on this finding, the inventor has shown that administration of a blackcurrant extract may increase cGP levels and/or cGP to total IGF-1 ratio hence ameliorating the effects of stroke, treating stroke or at least reducing the symptoms associated with stroke and/or other neurological conditions.

A further example of a neurological condition evaluated by the inventor is Parkinson disease (PD) which is the second most common neurodegenerative condition. As aforementioned, insulin-like growth factor-1 (IGF-1) is a neurotrophic factor and plays an essential role in neuronal survival and brain function. IGF-1 resistance, characterized as increase of circulating IGF-1 with impaired IGF-1 function, plays a role in disease progression of idiopathic PD, cognitive impairments and pathology of PD. Thus, changes of plasma concentration of IGF-1 also have been evaluated by the inventor as a biomarker for monitoring IGF-1 function, in order to predict the prognosis and treatment response in PD.

For the purposes of this specification, the terms 'amelioration', 'treat' or 'reduce the symptoms of' refers to reducing the measured impact of at least one indication or symptom associated with a neurological condition by at least 1, or 2%, or 3%, or 4%, or 5%, or 6%, or 7%, or 8%, or 9%, or 10% compared to that measured in the patient with no blackcurrant extract administration.

Administration may halt a decrease in cGP concentration or decrease in cGP to total IGF-1 ratio as a result of a non-normal state such as that caused by disease or a condition or from symptoms associated with a disease or condition. The term 'halt a decrease' as used refers to the cGP concentration and/or cGP to total IGF-1 ratio remaining within at least 1, or 2%, or 3%, or 4%, or 5%, or 6%, or 7%, or 8%, or 9%, or 10% of a measured concentration or ratio prior to administration.

Administration may increase cGP concentration and/or cGP to total IGF-1 ratio by at least 1, or 2%, or 3%, or 4%, or 5%, or 6%, or 7%, or 8%, or 9%, or 10% above what would be measured in the patient with no blackcurrant extract administration (BCA). The inventor has unexpectedly found that there may be a 25% increase of cGP in the cerebrospinal fluid (CSF) after BCA supplementation. Without being bound by theory, this suggests effective uptake by the brain following oral administration and is a significant finding for treatment of any brain diseases. Furthermore, BCA may increase the formation of cGP in human blood plasma. As far as the inventor is aware, there have been no other studies which have shown an effective brain uptake of at least 25% cGP in the CSF. Further clinical trials are in progress to confirm the efficacy and uptake of BCA supplementation. Also, elucidation of the mechanism may provide essential scientific evidence to further support BCA as an intervention for normalising IGF-1 function.

The animal referred to in the above aspects may be a human. The animal may alternatively be a non-human animal. Reference to an animal may used interchangeably herein with the words 'subject' or 'patient' and reference to one or the other should not be seen as limiting.

In one embodiment, the animal to which the blackcurrant extract is administered may be a healthy animal not exhibiting any non-normal cGP and/or cGP to total IGF-1 ratio. In this embodiment, the extract may be administered proactively as a means to prevent or avoid a change in cGP or cGP to total IGF-1 ratio that may in turn be associated with a disease, condition or symptoms of a disease or condition. Alternatively, the animal may have a pre-existing condition, disease state, and/or symptoms associated with a condition or disease state.

As noted above, terms such as 'normal' and 'healthy' are subjective terms however, in the context of this specification, the terms are a relative measure of the biomarker compound or ratio noted compared to either historical details about the animal and/or variation to a population referred to as a baseline or standard. The baseline of individual may vary between age, gender, and any other medical conditions that may be associated with IGF-1 function. It has been found that the changes of cGP and/or cGP to total IGF-1 ratio from the baseline of an individual is more critical information for guiding treatments and BCA dosage regimes. An exemplary study conducted by the inventor showed cGP level in plasma to be 3.5 ng/mg in healthy women, 8-10 ng/ml in 50-70 years of age and 12 ng-15 ng/ml in PD patients due to IGF-1 resistance.

The medicament described may be formulated in one embodiment for oral administration. Oral administration is a non-invasive and simple means to administer bioactive compounds and a method well explored in terms of blackcurrant. In addition, for the purposes of regulatory approvals, it may be a useful approach to make for marketing the method described. Despite reference to oral administration, the medicament could also be formulated for parenteral administration, for example non-limiting examples being as an injection, sublingual wafer or suppository. Overcoming the blood brain barrier (BBB) has been described extensively in the art for many bioactive compounds hence, some digression in whether oral or parenteral methods are preferred or even whether the BBB will allow transfer. The inventor has found that oral administration of the blackcurrant extract does cross the blood brain barrier and hence may be useful means for administration.

The extract itself may in one embodiment be a dried powder. The extract powder may be micronized to a diameter in the micron range. The extract may have a particle size of less than 1000, or 100, or 10, or 1 micron. The medicament comprising the extract may be formulated as a pill, tablet, capsule, liquid, powder, micronized powder, gel, soft gel full of liquid and combinations of these forms. Art blackcurrant extracts may be coarse powders with a particle size great than 1000 micron. Such extracts can be difficult to solubilise in aqueous environments and hence, micronized forms of the extract noted may be useful since they are easier to solubilise and hence more rapidly and more completely ingested and moved to the animal bloodstream.

As noted above, the dose is a therapeutically effect amount. In one embodiment, a therapeutically effective dose of blackcurrant extract may provide a dose of at least 50, 100, or 150, or 200, or 250, or 300, or 350, or 400, or 450, or 500, or 550, or 600, or 650, or 700, or 750, or 800, or 850, or 900, or 950, or 1000 mg of anthocyanins to the animal per day. The dose may be from 50 to 1000 mg, or 120 to 700 mg, or 200 to 700 mg, or 300 to 600 mg anthocyanins to the animal per day. As should be appreciated, the dose used may vary depending on factors such as individual animal metabolism, animal species, animal bodyweight, animal age and other factors, hence these doses should not be seen as limiting.

The blackcurrant extract may be derived from any blackcurrant variety grown internationally including, but not limited to Americas, Asia, Australia, Europe, and in New Zealand.

The blackcurrant extract may be derived from fruit grown in the Northern Hemisphere at latitudes above 40 degrees and/or in the Southern Hemisphere north of 50 degrees from the Equator.

In one embodiment, the blackcurrant plant may be from the species *Ribes nigrum*.

The blackcurrant extract described may be produced using fruit or fruits parts selected from: skins, juice, seeds, stalks, and combinations thereof. In one embodiment, the extract may be produced by maceration and enzyme digestion of the fruit including skins, juice, seeds and potentially leaf or stalk matter from the black currant plants, followed by drying to form a concentrated powder that may then be micronized. The micronized powder may optionally be encapsulated if a capsule form is desired or otherwise processed to a final form. In another embodiment, blackcurrant concentrate and/or single strength juice may be a source of cGP. Preferably, the blackcurrant concentrate may be up to 65 brix concentrate. The Applicant has found that a concentrate greater than 65 brix is too viscous.

The blackcurrant extract described may be produced from fruit harvested from at least one blackcurrant variety grown in New Zealand. New Zealand grown blackcurrants have an atypical composition compared to blackcurrants grown in other parts of the world and are somewhat unique in that they may have higher than usual anthocyanin levels. This may be due to: New Zealand's temperate climate of warm but not too warm summers (10-30° C. diurnal temperatures) and cool but not too cool winters (−5-15° C. diurnal temperatures); increased sun/UV radiation intensity, particularly during blackcurrant fruit ripening when the ozone layer is at a low over New Zealand; and, local 'terroir' where the blackcurrants are grown. The blackcurrants may be grown in the South Island of New Zealand.

However, this should not be seen as a limitation on the embodiments envisaged for this invention. Other types of organic or plant based material such as berry fruits, nuts, plants, bushes and the like containing a concentration of cGP and/or combinations thereof could conceivably be used with this invention. Also, these organic or plant based materials may contain any or minimal amounts of Anthocyanins. Non-limiting examples may include cranberry, beetroot, black elderberry and a BHC complex (bilberry and horse chestnuts), purple carrot, pine bark, beetroot, and purple wheat.

In one embodiment, the blackcurrant extract may be derived from fruit harvested from at least one 'Ben' blackcurrant variety. However, all other blackcurrant varieties may be used to form the extract. As may be appreciated, by mixing varieties yield, anthocyanin quantities and anthocyanin type may be varied and/or tailored in the extract. In one embodiment, the blackcurrant extract may be produced from fruit harvested from blackcurrant plants derived from the 'Ben Ard' variety, the 'Ben Rua' variety, and combinations of these varieties, or other blackcurrant varieties.

The blackcurrant extract described above may comprise at least 10 or 11 or 12 or 13 or 14 or 15 or 16 or 17 or 18 or 19, 20, or 21, or 22, or 23, or 24, or 25, or 26, or 27, or 28, or 29, or 30, or 31, or 32, or 33, or 34, or 35% and up to 50% by weight anthocyanins.

The blackcurrant extract may comprise Cyclic glycine-proline (cGP) in a concentration of at least 0.16 ng/mg and/or at least the required amount of cGP to deliver a health benefit.

The blackcurrant extract may be further characterised by comprising the anthocyanins: delphinidin-3-glucoside, delphinidin-3-rutinoside, cyanidin-3-glucoside, cyanidin-3-rutinoside, petunidin-3-rutonioside, and combinations thereof. Note that these same compounds may be referred to in the art literature as delphinidin-3-O-glucoside, delphinidin-3-O-rutinoside, cyanidin-3-O-glucoside, cyanidin-3-O-rutinoside, petunidin-3-O-rutonioside, the 'O' referring to the glycoside being linked by an oxygen atom. Another name for the same compounds may use the 'D' nomenclature to specify the direction the compound rotates in polarised light e.g. delphinidin 3-O-beta-D-glucoside. Reference to only the '3' form and absence of reference to 'O' or 'D' nomenclature should not be seen as limiting for the purposes of this specification.

The combination of the anthocyanins noted being delphinidin-3-glucoside, delphinidin-3-rutinoside, cyanidin-3-glucoside and cyanidin-3-rutinoside may comprise at least 80 to 90, or 91, or 92, or 93, or 94, or 95, or 96, or 97, or 98, or 99% by weight of the total amount of anthocyanin in the extract. That is, further anthocyanins may be present however, the extract used predominantly comprises that noted anthocyanins. Whilst not being bound by theory, it is understood that these anthocyanins, either in combination or separately, may be attributed to the observed effect in vivo on the binding of IGF-1 and hence the observed increase in cGP concentration and/or cGP to total IGF-1 ratio. That said, the extract comprises other compounds besides anthocyanins and, being derived from a plant, there may be other bioactive compounds or synergies from the extract not purely attributable to these compounds. As a result, reference to these compounds specifically is not intended to exclude the bioactivity of other compounds possibly present in the extract.

In one particular embodiment, the extract may comprise the following anthocyanin compounds, all as measured and for a standard New Zealand anthocyanin analysis comprises, as measured in unconcentrated juice from the blackcurrants:
at least 60 mg/100 ml delphinidin-3-glucoside; and/or
at least 200 mg/100 ml delphinidin-3-rutinoside; and/or
at least 40 mg/100 ml cyanidin-3-glucoside; and/or
at least 240 mg/100 ml cyanidin-3-rutinoside; and/or
The extract may further comprise at least 14 mg/100 ml petunidin-3-rutonioside as measured in unconcentrated juice obtained from blackcurrant fruit.

Advantages of the above may be varied. With respect to a biomarker, cGP as noted is a stable metabolite of IGF-1 and based on the inventor's work, is easily measured in biological specimens taken from an animal. cGP is formed from an unbound active form of IGF-1 and hence is more reliable than measuring total IGF-1. With respect to the described methods of increasing cGP and/or addressing neurological conditions, the use of blackcurrant in such as measurable and known manner has not been known or completed in the art. Blackcurrant juice or other forms of blackcurrant (not the extracts noted) have not been used in the known and measurable manner now possible and as described herein. The stroke and PD findings in particular exhibit a new or at least alternative use for blackcurrant that may provide significant and measurable benefit to patients potentially also without interfering with existing art treatments or causing unwanted side effects. It should be noted though; the inventor has found that Vitamin C, if added to BCA as ascorbic acid, has a negative effect on the efficacy when applying BCA to increase the levels of cGP.

With respect to the described methods of measuring the changes in cGP and/or addressing neurological conditions, an advantage of the clinical application of cyclic glycine-proline (cGP) as a reliable biomarker allows for selection of suitable patients for treatment and individual dosage regimes. The increase of cGP indicates the risk of a neurological condition and the reduction of cGP indicates the stage of the neurological condition. Advantageously, suitable patients for treatment may be selected based on their cGP level and the changes of cGP levels can be easily monitored for a tailored or personalised treatment dosage regime. Adjusting the dosage regime of BCA allows for effective treatment of the neurological conditions, thus improving long-term recovery (beyond 3 months) and prevention of long time complications (cognitive impairment) associated with neurological conditions. A further advantage is that cGP levels can simply be monitored by measuring urine samples for ease of analysis and critical for large scale clinical trials of BCA in the future.

Further, with respect to natural products and associated bioactive compounds generally, the methods and uses described herein provide unique ways to know when it is appropriate to intervene with a treatment and further, provide ways to measure the success or otherwise of a treatment. This insight into timing and efficacy is something many pharmaceutical drugs would aspire to and not something commonly observed in natural products containing bioactive compounds.

The embodiments described above may also be said broadly to consist in the parts, elements and features referred to or indicated in the specification of the application, individually or collectively, and any or all combinations of any two or more said parts, elements or features.

Further, where specific integers are mentioned herein which have known equivalents in the art to which the embodiments relate, such known equivalents are deemed to be incorporated herein as of individually set forth.

WORKING EXAMPLES

The above described methods relating to the clinical application of cyclic glycine-proline (cGP) biomarker for prediction of risk and recovery of non-neurological and neurological conditions and the use of a cGP containing organic or plant based material such as a concentrated extract of blackcurrant anthocyanins (BCA) for the treatment of same are now described by reference to specific examples.

Example 1

A trial was completed by the inventor to see if supplementation of blackcurrant anthocyanins (BCA) increased cyclic glycine-proline (cGP) in the cerebrospinal fluid (CSF) of Parkinson patients; a trophic response to improve the function of insulin-like growth factor-1 (IGF-1).

Biological specimen samples were taken from patients and the specimens analysed for cGP and cGP to total IGF-1 ratio to confirm whether or not cGP and cGP to total IGF-1 ratio may be used as a predictor of active IGF-1 presence and function. The trial then went on to analyse the effects of blackcurrant extract supplementation on cGP in patients.

All patients were recruited form the Van der Veer Movement Disorders clinic and from the patient database of New Zealand Brain Research Institute. Patients were eligible to enroll in the study irrespective of the stage of disease and time since diagnosis. The patients were aged 40 years or older and met the UK Brain Bank criteria for idiopathic PD confirmed by a movement disorders neurologist. The study was approved by the Upper South A Regional Ethics Committee (reference: URA/10/03/022). A flowchart of Study population shows the patients recruiting. Patients were assessed using the Unified PD Rating Scale (UPDRS) parts III and also administered a battery of psycho-cognitive tests before obtaining the samples at first visit. These included the HADS, the Mini Mental State Examination (MMSE), the Montreal Cognitive Assessment (MoCA) and the PD Questionnaire (PDQ-39). To avoid any learning effects different versions of the tests were used for the second visit if available. Table 1 shows the clinical information and assessments of the patients prior to the trial. The majority of patients were diagnosed as idiopathic PD without obvious cognitive impairment.

TABLE 1

Clinical information of 10 PD patients before BCA supplementation

| Case | Age | Clinical Diagnosis | UPDRS III | MMSE | MoCA | HADS | PDQ-39 |
|---|---|---|---|---|---|---|---|
| BM02BC | 61 | idiopathic PD | 15 | 29 | 29 | 6 | 43.75 |
| LE14BC | 77 | idiopathic PD | 48 | 27 | 22 | 3 | 31.25 |
| SE07BC | 73 | idiopathic PD | 36 | 30 | 24 | 9 | 90.63 |
| YY03BC | 48 | idiopathic PD | 33 | 29 | 29 | 8 | 59.83 |
| EK05BC | 80 | idiopathic PD | 52 | 29 | 27 | 6 | 156.25 |
| GD08BC | 80 | idiopathic PD | 34 | 28 | 24 | 11 | 134.88 |
| ED12BC | 60 | idiopathic PD | 33 | 30 | 25 | 3 | 65.63 |
| EY17BC | 56 | idiopathic PD | 27 | 30 | 28 | 21 | 159.38 |
| TN15BC | 70 | idiopathic PD | 51 | 28 | 22 | 21 | 250 |
| KT16BC | 55 | idiopathic PD | 31 | 28 | 26 | 4 | 71.88 |

HADS, Hospital Anxiety and Depression Scale; MMSE, Mini-mental State Examination; MoCA, Montreal Cognitive Assessment; PDQ-39, Questionnaire; UPDRS-III, Unified Parkinson Disease Rating Scale-part three.

The trial method comprised taking seven pairs of cerebrospinal fluid (CSF) samples from 7 male volunteers both before supplementation and 28 days post blackcurrant extract supplementation.

During each visit plasma and cerebrospinal fluid (CSF) samples were collected. Patients were instructed to consume a "low-anthocyanin diet" (i.e. white rice, white bread, tuna, chicken, coffee and non-herbal tea) 12 hours before each visit.

Following the first visit, patients were supplemented with blackcurrant capsules over the next 28 days. The dose of BCA concentrate capsules (20% anthocyanins, Super Currantex® 20, funded by Just the Berries Ltd. New Zealand (manufactured by NZ Pharmaceuticals Limited)) taken twice daily over a 28 day time period. The extract dose that each patient took was equivalent to approximately 600 mg anthocyanins per day. The extract was produced from New Zealand grown Ben variety fruit. The extract was produced by maceration and enzyme digestion followed by drying to form a concentrated powder that is then micronized and encapsulated.

As above, the volunteers were people having Parkinson's disease (PD) hence, they would already have some IGF-1 function challenges since IGF-1 is a neurotrophic factor and plays an essential role in neuronal survival and maintaining brain function possibly impaired in the PD patients leading to the symptoms observed such as tremors. IGF-1 resistance may be characterised by an increase in circulating IGF-1 and impairment of IGF-1 function has been reported to be associated with cognitive decline in PD patients. In circulation, IGF-1 is in storage and not functional. However, each IGF-1 molecule contains the small cGP molecule and a metabolite of IGF-1 which enables IGF-1 to be fully functional. cGP acts like a doorkeeper to decide the number of IGF-1 that can leave the storage and become a worker in one to one manner. Therefore, cGP increases in a patient's circulation when there is not enough functioning or working IGF-1 or when the body demands more working IGF-1. Hence cGP is important to enable IGF-1 to function at full strength and hence is neuroprotective through improving IGF-1 function.

Each sample was obtained and analysed to determine the total IGF-1, cGP and IGF binding protein 1-3 concentrations in each sample taken before and after supplementation. The samples were analysed using ELISA and High-Performance Liquid Chromatography (HPLC) mass spectrometry.

In Particular:

CSF Samples

CSF samples were obtained by lumbar punctures. Around 8 mL of CSF was obtained during each visit. The CSF sample, collected in a plain tube, was transported on wet ice to Endolab, Christchurch, New Zealand, within 15 minutes of collection. The samples were then centrifuged at 3000 rpm for 15 minutes at room temperature, and the supernatant was aliquoted equally between two plain tubes and frozen under $-80°$ C. within 30 minutes of sample-receipt.

Plasma Samples

Blood samples were obtained via venipuncture of the antecubital fossa; 20 mL were divided equally between a heparin and EDTA tubes. The samples were immediately transported on wet ice to Endolab within 45 minutes of collection. The samples were then centrifuged (3000 rpm) for 15 min, and the plasma was aspirated into a plain tube and frozen under $-80°$ C. within 30 minutes of sample-receipt.

In Vitro Samples

To analyse potential presence of cGP in the BCA, BCA was dissolved in water with 3 different concentrations of 5, 50 and 100 mg/ml. Each concentration has been analysed in five duplicates.

As described below in cGP Assays and HPLC-ms, the method of determining the level of cGP in BCA and other organic or plant based material.

cGP Assays cGP-$d_2$ provided an internal standard for cGP assay. cGP-$d_2$ (50 µL of 500 ng/mL) was added to 100 µL of plasma, vortex mixed. The solution was transferred to a 1 mL Phree phospholipid removal cartridge (Phenomenex, Auckland, New Zealand) contained in 4.5 mL tube; 500 µL of 1% formic acid in Acetonitrile (MeCN) was added to the cartridge and centrifuged at 1000 rpm for five minutes at 4° C. to enable the collection of the filtrate. The filtrate was dried using a vacuum concentrator (1.5 mTor for an hour, then 0.7 mTor for 45 minutes, at room temperature). The dried samples were reconstituted in 100 µL 10% methanol/water and transferred to a ultra-pressure liquid chromatography vial for quantitation, then centrifuged at 500 rpm for five minutes at 4° C. to sediment any remaining particulates. Standards prepared by spiking cGP into charcoal stripped human plasma, quality control samples, with cGP at two different concentrations, were utilized and then subjected to the same extraction procedure as the samples.

High Performance Liquid Chromatography Mass Spectrometry Assay (HPLC-Ms)

Briefly, the chromatography conditions consisted of a Synergy Hydro 2.5 µm column (Phenomenex) 100×2 mm with an initial mobile phase composition of 10% methanol/90% water flowing at 200 µL per minute with a column temperature of 35° C. The mass spectrometry conditions consisted of electrospray ionization in positive mode with a voltage of 4000 V, a sheath gas flow of 30 psi, an auxiliary gas flow of 2 psi, and a capillary temperature of 250° C. Fragmentation achieved with argon at 1.2 mTorr as the collision gas and a dissociation voltage of 35 V. The mass spectrometer ran in selective reaction monitoring (SRM) mode with the following two transitions 155.1→70.2 m/z and 157.1→70.2 m/z utilized for cGP and cGP-$d_2$, respectively. The retention time for both peaks was 3.6 minutes. Unknown samples were quantitated using the peak area ratio of cGP/cGP-$d_2$ compared with the standard curve of known concentrations.

ELISA

Plasma and CSF concentration of total IGF-1, IGFBP-1, -2 and -3 were measured using commercial ELISA kits (Crystal Chem, Chicago, IL, USA) according to manufacturer's instructions. The assays were repeated four times in plasma samples and but only duplicated in CSF samples due to the limited amount of CSF available.

Statistical Analysis

Paired t-test was used for analyzing the changes in cGP, IGF-1, IGFBP-1, IGFBP-2 and IGFBP-3 following blackcurrant supplementation. Correlations between the biological changes were calculated using Pearson tests. P-value less than 0.05 are considered to be significant.

Results

In Vitro Analysis of cGP Concentration in BCA

One-way ANOVA suggested the concentration of cGP was significant different between the different dose of BCA (p<0.0001, n=5, FIG. 1). Compared to the group with low BCA (5 mg/ml) the concentration of cGP was significantly increased in the group with 50 mg/ml BCA (p=0.0001, n=5) and further increased when the BCA dose increased to 100 mg/ml (p<0.0001, n=5).

CSF

Figure 2:
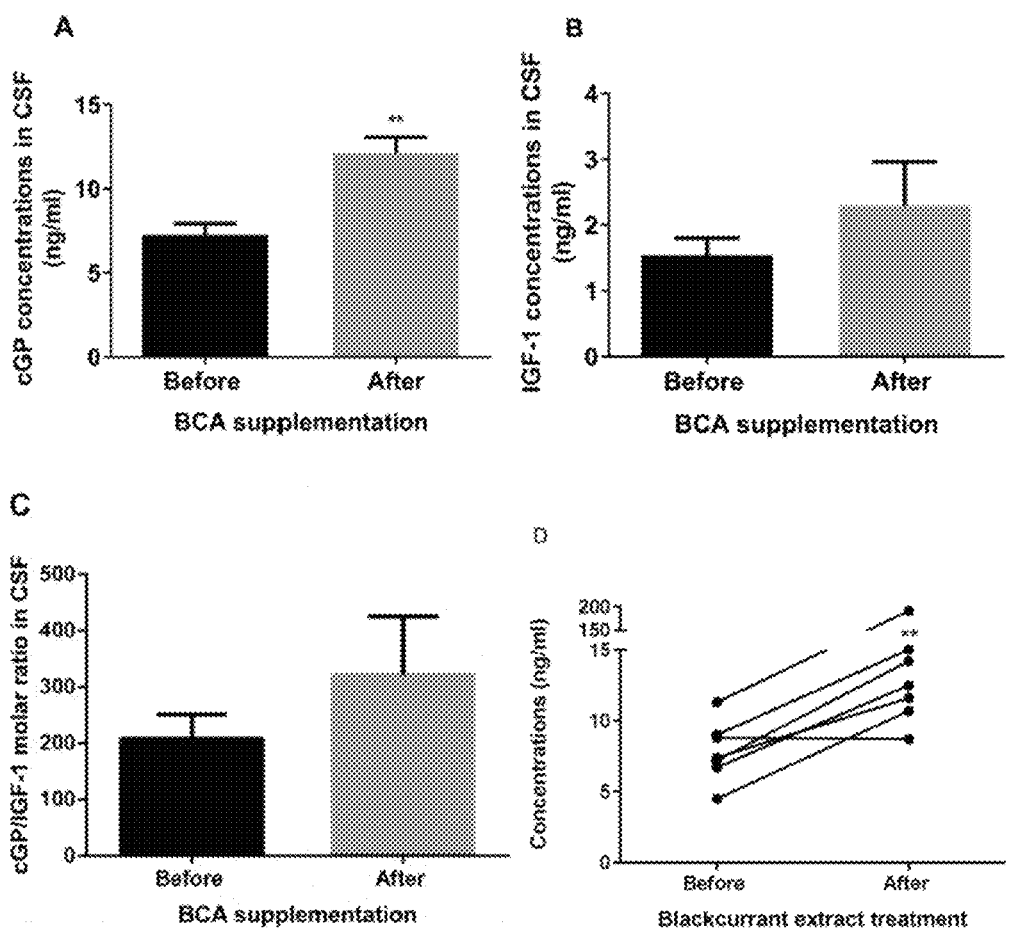
FIG. 2 shows graphs illustrating the changes of cGP (FIG. 2A), IGF-1 (FIG. 2B) and the ratio of cGP/IGF-1 (FIG. 2C) in patient CSF samples before and after blackcurrant extract supplementation. There was statistical difference in IGF-1 concentration and the cGP/IGF-1 ratio. Data presented as mean±SEM, $p<0.01$.

There was a significant increase in CSF cGP concentration after BCA supplementation (from 7.27±0.67 to 12.12±0.94, p<0.001, n=6, FIG. 2A). The mean percentage changes in cGP concentrations was increased by 74.36% after supplementation (p<0.05, t(5)=3.989. Amongst total seven pairs of samples, six of them showed an increase after supplementation. One patient showed 16.9 times increase (11.30 ng/ml to 191.80 ng/ml) of cGP in the CSF, which has been eliminated from the statistical analysis as an outlier (15.7 times of mean). One patient did not respond the supplementation with cGP concentration remained the same after the supplementation (from 8.8-8.7 ng/ml, FIG. 2D). There was no change in the concentration of IGF-1, cGP/IGF-1 ratio (FIGS. 2B and C), IGFBP-2 and IGFBP-3 (Table 2).

Plasma

There were no statistical changes in the concentrations of cGP, IGF-1, cGP/IGF-1 ratio (FIGS. 3A-C), IGFBP-1, 2 and -3 following BCA supplementation (Table 2).

CSF Vs Plasma Concentration

Table 2 shows the values for cGP, IGF-1 and IGFBPs in CSF and plasma before and after supplementation. The concentration of IGFBP-1 was low in plasma. IGFBP-3 (3038-3029 ng/mL) was the predominant IGFBP in plasma and IGFBP-2 (83.7-85.5 ng/mL) in CSF. The CSF/plasma ratio was <1% in both IGF-1 and IGFBP-3; was 1.3-2% in IGFBP-2 and 52-71% in cGP (Table 2).

Correlation Analysis

Figure 4:
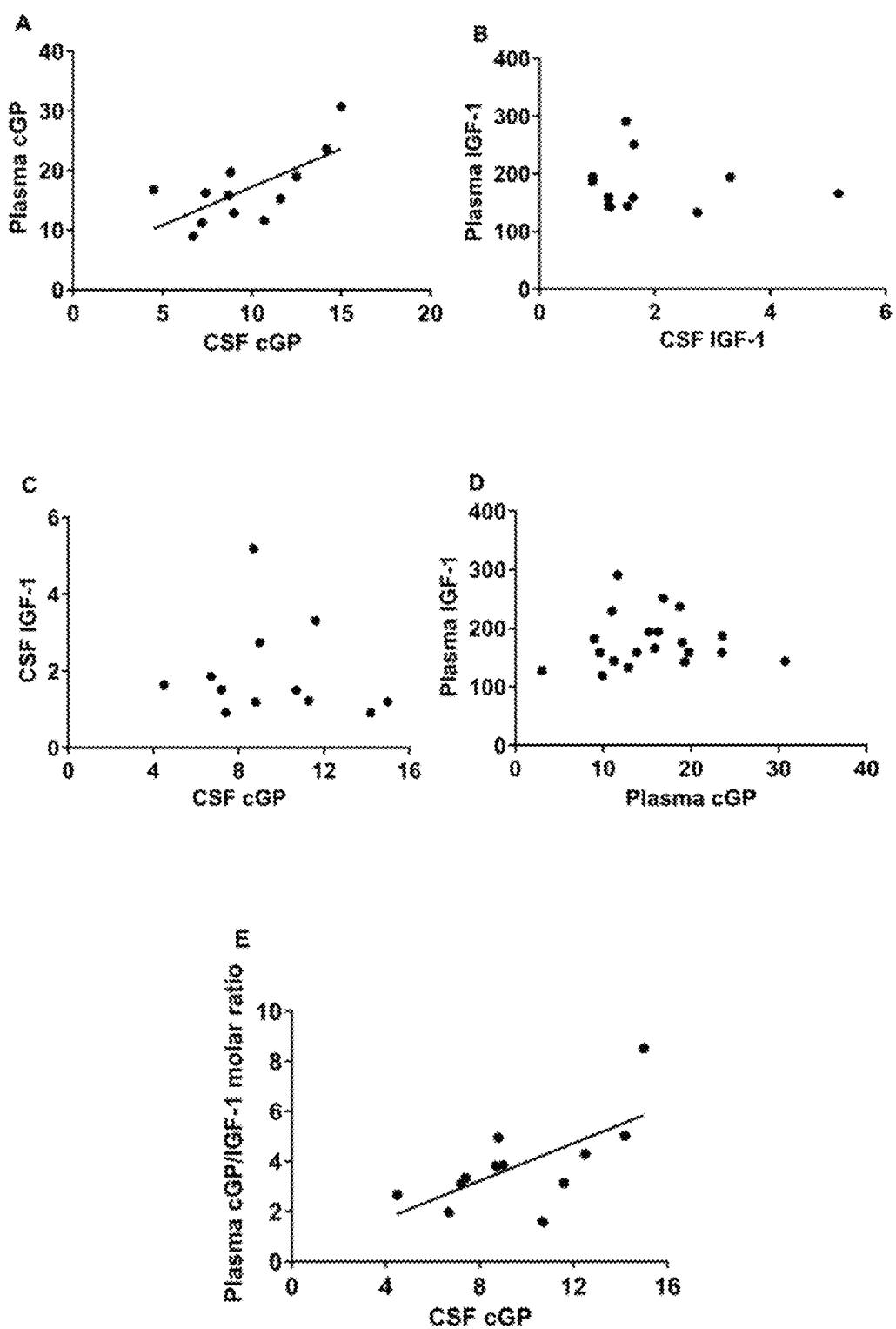
FIG. 4 shows graphs illustrating the correlation of between CSF cGP and plasma cGP concentration (FIG. 4A), between CSF IGF-1 and plasma IGF-1 concentration (FIG. 4B), between CSF cGP and CSF IGF-1 concentration (FIG. 4C), plasma cGP and plasma IGF-1 concentration (FIG. 4D) and between CSF cGP and plasma cGP/IGF-1 molar ratio (FIG. 4E). The concentration of CSF cGP is significantly correlated with plasma cGP (A, $r=0.68$, $p=0.014$) and plasma cGP/IGF-1 ratio (E, $r=0.66$, $p=0.016$). The cGP/IGF-1 ratio is also correlated with plasma cGP concentration (F, $r=0.9$, $p<0.001$). IGF-1 concentration was not correlated between the CSF and plasma (Figure B) and there was no correlation between cGP and IGF-1 concentration in CSF (FIG. 4C) and plasma (FIG. 4D)

Pearson tests revealed significant correlation between the concentrations of cGP in CSF and plasma (R=0.68, p=0.01 FIG. 4A, n=12), as well as between the ratio of cGP/IGF-1 in plasma and cGP concentrations in CSF (R=0.66, p=0.01, FIG. 4E, n=12). There was no correlation in IGF-1 concentration between the CSF and plasma (R=0.09, p=0.75, FIG. 4B), and no correlation between cGP and IGF-1 concentration in both CSF and plasma (R=0.04, p=0.85, FIG. 4D, R=−0.12, p=0.69 FIG. 4C).

The results summarised below in Table 2 show the measured data before and after supplementation.

TABLE 2

Measured Values for cGP, IGF-1 and IGFBP's in CSF Before and After Supplementation

|  | CSF (ng/mL) Mean ± SEM (n = 6) | Plasma (ng/mL) Mean ± SEM (n = 9-10) | Ratio of CSF to plasma (%) |
| --- | --- | --- | --- |
| Before the Supplementation | | | |
| IGF-1 | 1.54 ± 0.26 | 179.04 ± 14.89 | 0.86% |
| cGP | 7.27 ± 0.67 | 13.96 ± 1.33 | 52.01% |
| IGFBP-3 | 26.16 ± 2.79 | 3038.92 ± 111.90 | 0.86% |
| After the Supplementation | | | |
| IGF-1 | 2.29 ± 0.67 | 176.07 ± 14.13 | 1.30% |
| cGP | 12.12 ± 0.94 | 16.92 ± 2.79 | 71.63% |
| IGFBP-3 | 27.69 ± 3.53 | 3029.09 ± 59.35 | 0.91% |

DISCUSSION

Figure 3:
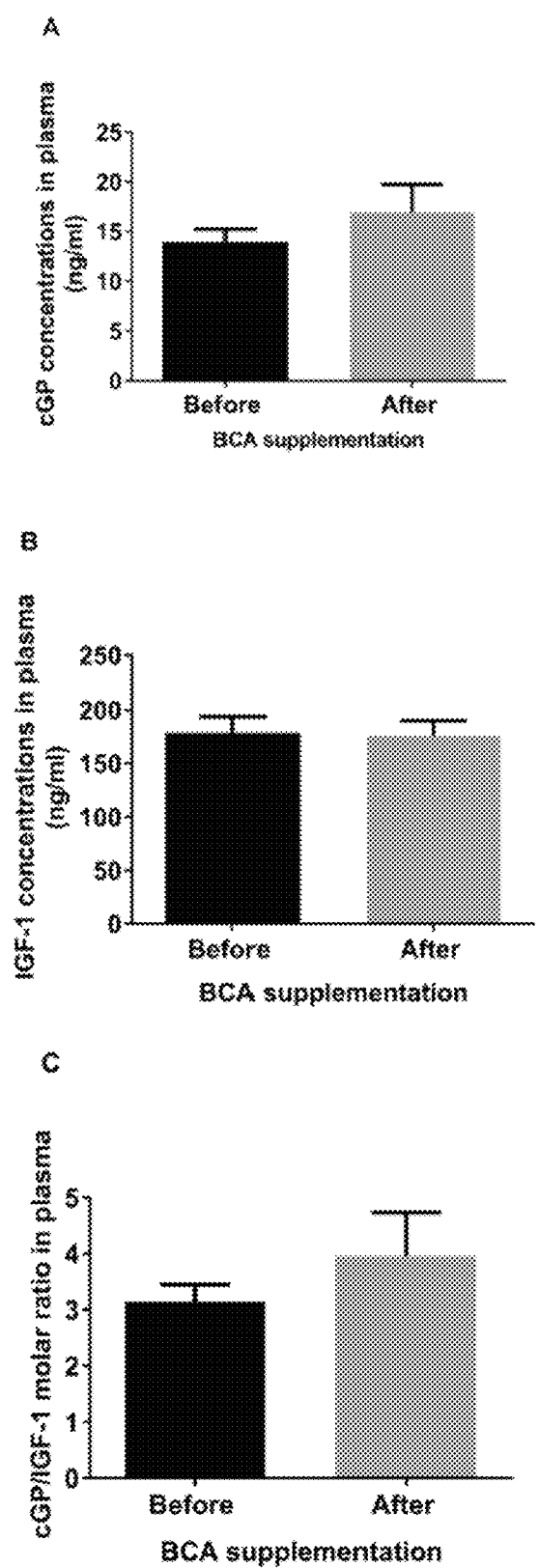
FIG. 3 shows graphs illustrating the changes of cGP (A), IGF-1 (FIG. 3B) and the ratio of cGP/IGF-1 (FIG. 3C) in the plasma following supplementation of BCA. There was no statistical change in cGP, IGF-1 concentration or cGP/IGF-1 ratio. Data presented as mean±SEM.

As has been found, BCA comprises cGP is a nature nutrient. The supplementation of BCA led to an increase of cGP, but not IGF-1 in the CSF of PD patients. The cGP concentration in the CSF correlated with cGP concentration and the ratio of cGP/IGF-1 in the plasma, even though the changes in the plasma were not significant. The central uptake from plasma was high in cGP and low in IGF-1 and IGFBPs possibly due to the function of blood-brain barrier (BBB). The increase of cGP in the CSF may be a trophic response to the BCA supplementation. The non-statistical change of plasma cGP was a likely cause. Elucidating the mechanism will provide further scientific evidence that BCA may be an intervention for normalising IGF-1 function.

cGP is a small and lipophilic molecule (192d), with the ability to cross the BB. Approximately 52% of plasma cGP was found in the CSF before the supplementation and increased to 71% after the supplementation (Table 2), leading to significant correlation of between CSF and plasma concentration of cGP (FIG. 3A). Thus, plasma cGP was a likely source for the increase of CSF cGP, even though the supplementation did not significantly increase cGP concentration in plasma. There was no correlation between cGP and IGF-1 in CSF (FIG. 3C), which may not exclude a possibility that a small part of CSF cGP forms from IGF-1 in the central nerve system (CNS) as the enzyme cleaving IGF-1 also occurs in the CNS.

In contrast to cGP, the concentration of IGF-1 in the CSF was about 1% of plasma IGF-1 (Table 2) and there was no correlation between them (FIG. 3B). These observations suggest that CSF IGF-1 was largely independent from circulating IGF-1. IGF-1 is a larger molecule (7600d) than cGP, with limited ability to cross the BBB. The data showed that the central uptake of cGP was high and IGF-1 was low, due to the maintained function of the BBB in the PD patient sampled. Without being bound by theory, it is possible that the demand for trophic supports from degenerating brains promoted cGP transfer from plasma to CSF. Thus further increase of CSF cGP after supplementation of anthocyanin may be a trophic response to BCA treatment in order to improve IGF-1 function. Given that cGP is a nature nutrient of BCA, the beneficial effect of BCA may be mediated through improving bioavailable IGF-1, thus its function. Although the changes of CSF cGP were significant, further clinical trials with larger number of cases will confirm the efficacy of BCA supplementation, particularly the changes of cGP in plasma.

Conclusion

In conclusion, cGP is a nutrient of BCA and the supplementation of BCA lead to the elevation of cGP in the CSF of PD patients, in order to improve IGF-1 function in PD brains. For example, BCA supplementation significantly increased CSF concentration of cGP after supplementation (p<0.001, n=7) as shown in FIG. 2A. The ratio of cGP/IGF-1 also changed significantly as shown in FIG. 2C.

The increase of cGP in the CSF was likely a result of high central uptake of plasma cGP. The central uptake of IGF-1 was limited due to retained BBB function in PD patients. The changes of cGP and cGP/IGF-1 ratio in plasma might provide additional indication for IGF-1 function in degenerative brains, and will be further evaluated in a large clinical trial.

By contrast, supplementation did not significantly alter the concentration of IGF-1 in the CSF (FIG. 2B) samples reiterating the fact that measuring IGF-1 or bound IGF-1 is a poor biomarker as it does not allow distinction of IGF-1 function (active or bound) and hence cannot reliably be used as a measure of IGF-1 activity.

Example 2

In this Example, the ability to use cGP as a biomarker was further evaluated. A total of 29 people were recruited for the trial, the patients being aged either over 70 years old or under 70 years old, all with normal cognitive function. Biological specimens in the form of plasma were taken from the patients.

The concentration of IGF-1 and IGFBP-3 in the plasma was measured by ELISA and plasma cGP was measured by High Performance Liquid Chromatography mass spectrometry assay.

Figure 5A:
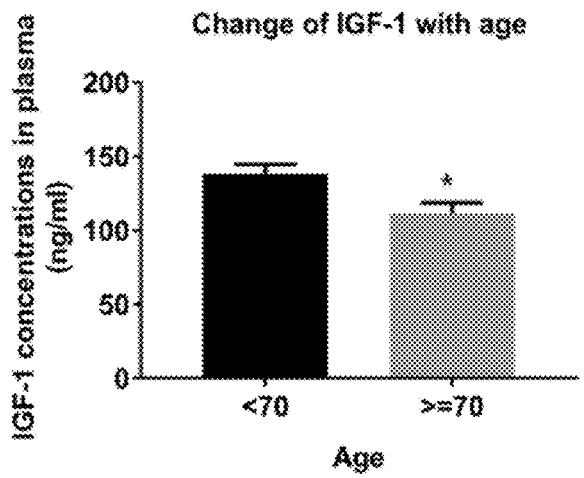
FIG. 5 illustrates graphs showing the measured changes of cGP and cGP/IGF-1 with age. Compared to the group under 70 years of age (<70, Black bars) IGF-1 reduced in older group (FIG. 5A, >=70, Grey bars), whereas the cGP concentration and cGP/IGF-1 ratio increased in the older age group (FIG. 5B and FIG. 5C, >=70). Data are presented as mean±SEM and $p<0.05$.
Figure 5B:
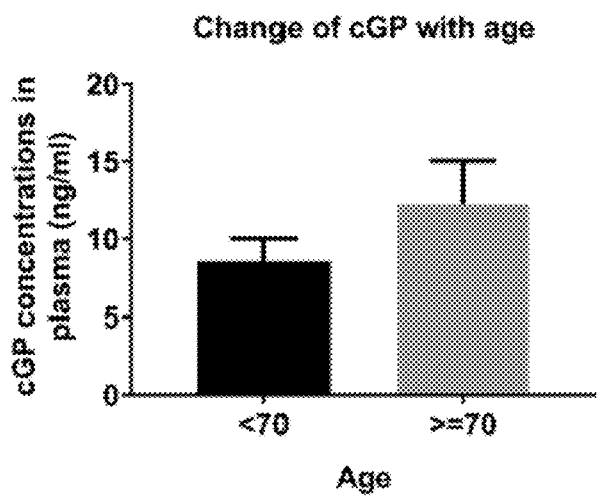
Figure 5C:
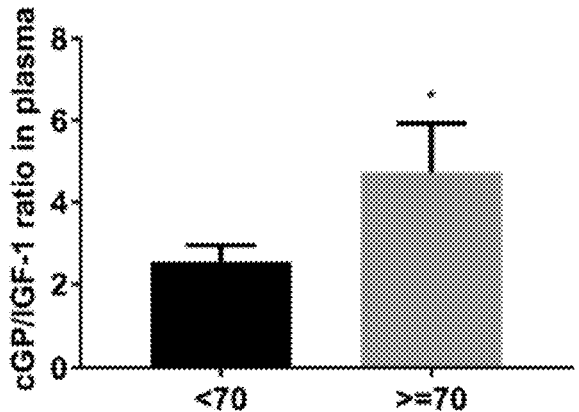

The results were as shown in FIGS. 5A, 5B and 5C.

FIG. 5A illustrates how the total plasma IGF-1 measured concentration tends to decrease with age but the differences in measured total IGF-1 were relatively small.

By contrast, FIG. 5B shows how cGP plasma concentration changes with age, the change being pronounced and easy to measure. FIG. 5C further shows how the measured cGP to total IGF-1 ratio also changes significantly with age.

Without being bound by theory, it is speculated that observed increase in cGP and cGP/IGF-1 ratio is a compensatory response to the reduced plasma IGF-1 in order to maintain normal cognition in older people.

Example 3

In this Example, an initial trial was completed to test the clinical application of cGP biomarker for prediction of risk and recovery of stroke for individual treatment regimes.

(Note that a completed updated trial is now described in Example 8 with updated data and Figures, where baseline measurements were amended to 72 h as during the study there were not enough patients admitted to the hospital <48 h after stroke. Also, the baseline data of mRS is no longer utilised as this data was not as reliable <3 days after stroke and has been replaced with NIHSS).

It is understood that IGF-1 function is important for stroke recovery. As a result, a reliable biomarker for IGF-1 function in stroke may be useful for prognosis of stroke. However, as noted elsewhere in this specification, plasma IGF-1 or IGF-1/IGF binding protein-3 (IGFBP-3) ratio are not reliable biomarkers. cGP was tested as a potential biomarker for IGF-1 function during spontaneous recovery of stroke patients.

Plasma samples were collected from 14 stroke patients at baseline (<48 h), 1 week and 3 months from stroke onset. Moreover, 29 plasma samples were collected from age-matched healthy people to act as negative controls for the trial.

Functional recovery after stroke was evaluated using the difference in modified rank scale (mRS) between baseline and 3 months ($\Delta$mRS). The concentration of IGF-1 and IGFBP-3 in the plasma samples were measured by ELISA and plasma cGP was measured by High Performance Liquid Chromatography mass spectrometry assay.

Figure 6A:
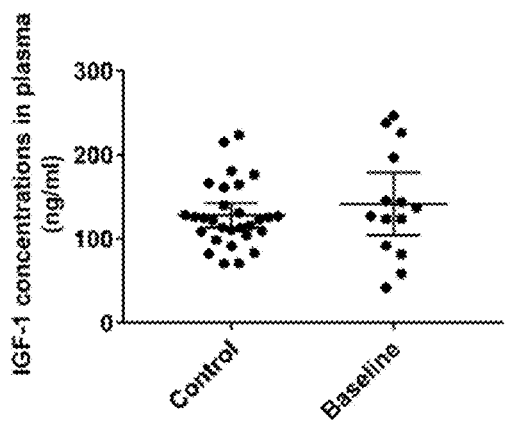
FIG. 6 illustrates graphs showing measured changes of cGP (FIG. 6C), IGF-1 (FIG. 6A), IGFBP-3 (FIG. 6B) and c-GP/IGF-1 ratio (FIG. 6D) between normal control (no stroke) and base-line level of stroke patients (correlates with updated data presented in FIG. 15)

The results showed no changes in plasma IGF-1, this result further reiterating the poor nature of IGF-1 as a biomarker (FIG. 6A). By contrast, stroke patients had significantly lower cGP levels (p=0.006, FIG. 6C) and c-GP/IGF-1 ratio (p=0.001. FIG. 6D) compared with healthy patient controls.

Figure 6B:
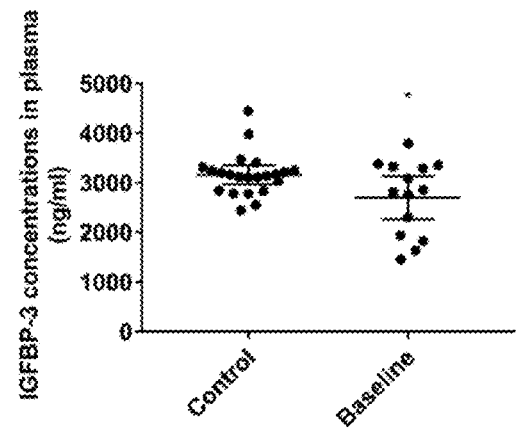
Figure 6C:
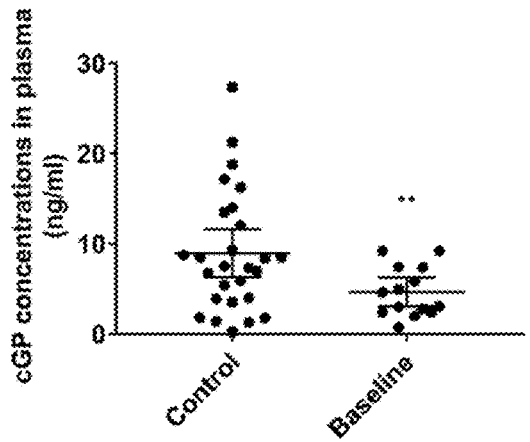
Figure 6D:
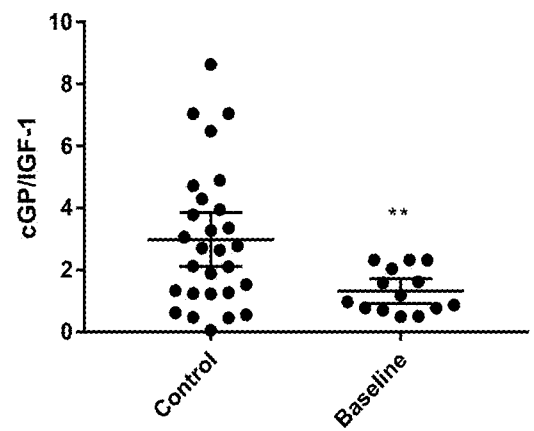

IGFBP-3 slightly declined in stroke patients (p=0.049, FIG. 6B). The reduced the IGFBP-3 could be a positive response to increase free IGF-1.

The change in cGP and its ratio to IGF-1 are therefore more sensitive biomarkers for IGF-1 function during stroke recovery than reliance on IGF-1 measurement alone.

Of interest was the significantly reduced cGP concentration within 48 h of stroke onset. It is uncertain if this sudden decrease is a direct result or the cause of stroke but this appears to be an observable characteristic and perhaps an indicator of abnormal function.

Figure 14:
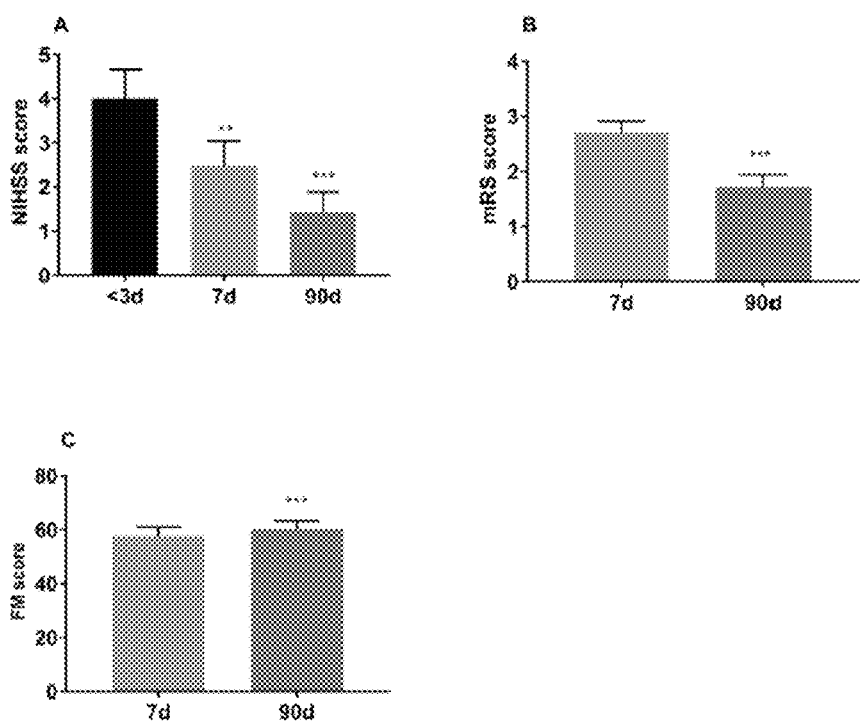
FIG. 14 illustrates graphs showing that the study stroke patients made recovery from 3, 7 and 90 days respectively by showing significant decrease in neurological scores (NIHSS, FIG. 14A), (mRS, FIG. 14B) and improvement in FM scores (FIG. 14C)

The result taken over time as illustrated in FIG. 7A to 7E (see also updated FIG. 14) showed that the stroke patients made gradual recovery over 3 months by showing reduced mRS (FIG. 7A)—now equivalent to updated NIHSS as shown in Table 7). Compared with the baseline level (<48 h after stroke), there was a trend in the stroke patients towards an increase in cGP (p=0.057, n=14) and c-GP/IGF-1 (p=0.08, n=14, FIG. 7B and FIG. 7E) at 3 months.

Figure 7A:
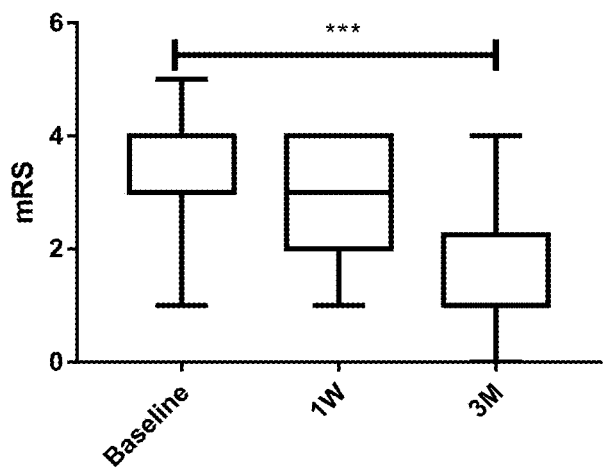
FIG. 7 illustrates graphs showing that the study stroke patients made recovery over 3 months by showing significant decrease in neurological scores (FIG. 7A). There was a trend toward an increase in plasma cGP (FIG. 7B) and cGP/IGF-1 ratio (FIG. 7E). The baseline cGP concentration is correlated with the recovery of stroke (FIG. 7F). There were no changes in IGF-1 and IGFBP-3 (FIG. 7C and FIG. 7D) over the period of stroke recovery (correlates with updated data presented in FIG. 16)
Figure 7B:
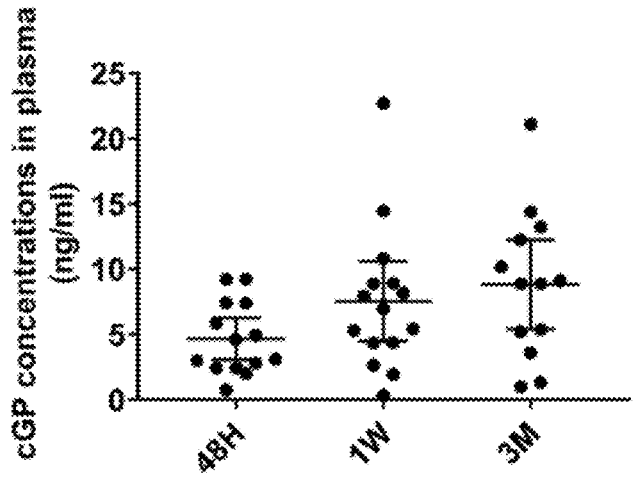
Figure 7C:
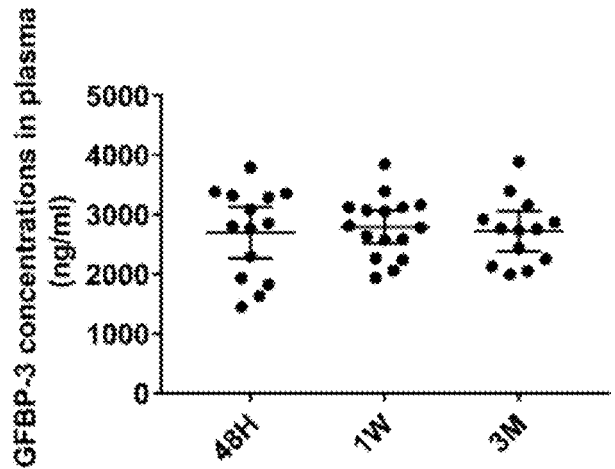
Figure 7D:
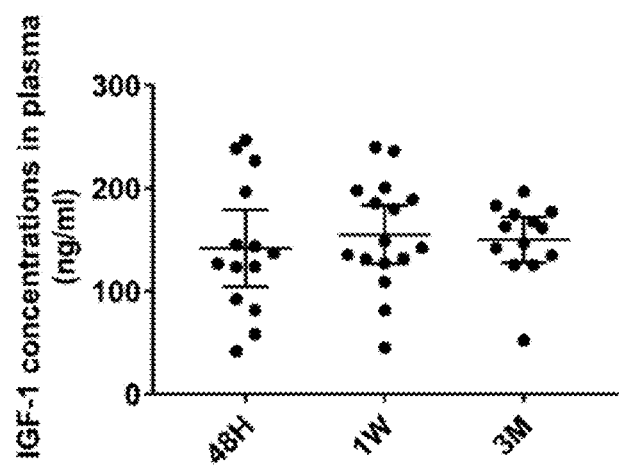
Figure 7E:
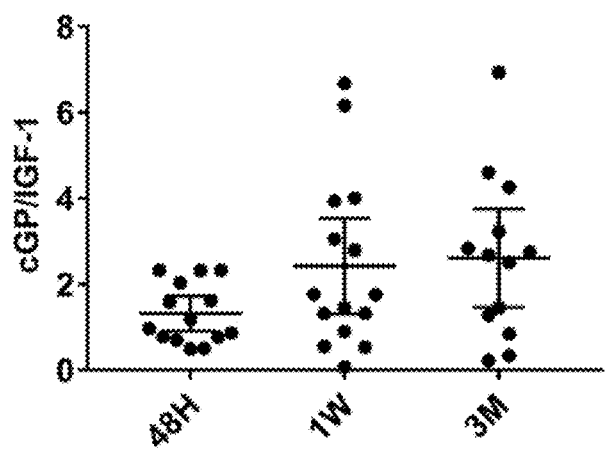
Figure 7F:
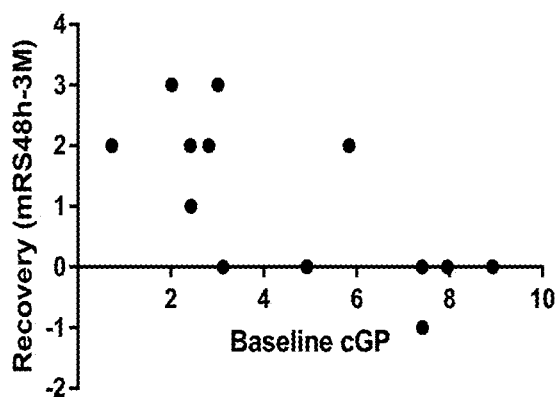

Baseline cGP was negatively associated with recovery, evaluated by the differences in neurological scores between baseline and 3 months ($\Delta$mRS, r=−0.651, p=0.022, FIG. 7F).

The inventor's results suggest that baseline cGP may predict the short-term outcome of stroke recovery. The greater the baseline cGP the more positive the prognosis for the patient. The results also further support the initial finding that changes of cGP and cGP/IGF-1 ratio may be a more reliable biomarker than IGF-1 and IGF-1/IGFBP-3 ratio since there were no changes in IGF-1 and IGFBP-3 over the period of stroke recovery.

Increase in cGP is understood to be a trophic response to promote stroke recovery. Similar to the increase of cGP and the ratio of cGP/IGF-1, the increased cGP during stroke recovery is also understood to be a trophic response to promote stroke recovery. These findings indicate that recovery may be correlated with cGP and supplementation of cGP may assist recovery. Further, since the cGP concentration at 48*h* after stroke is significantly correlated with the recovery of neurological function in the stroke patients (FIG. 7F), this suggests that the cGP concentration at the time of admission to hospital may predict the ability of recovery, thus critical information for treatment. This also would suggest that supplementation to increase cGP levels may also help with short term recovery from stroke.

Example 4

In the trial noted above, urine samples were also taken from the patients enrolled in the study to test if urine would also be a useful biological specimen. A total of 71 urine samples were taken during the study (30 controls, 33 stroke patients) and these samples were analysed in a similar manner to the above methods. To confirm that a correlation exists, an additional 37 plasma samples in stroke patients and aging controls from the earlier trial were also compared.

Figure 8:
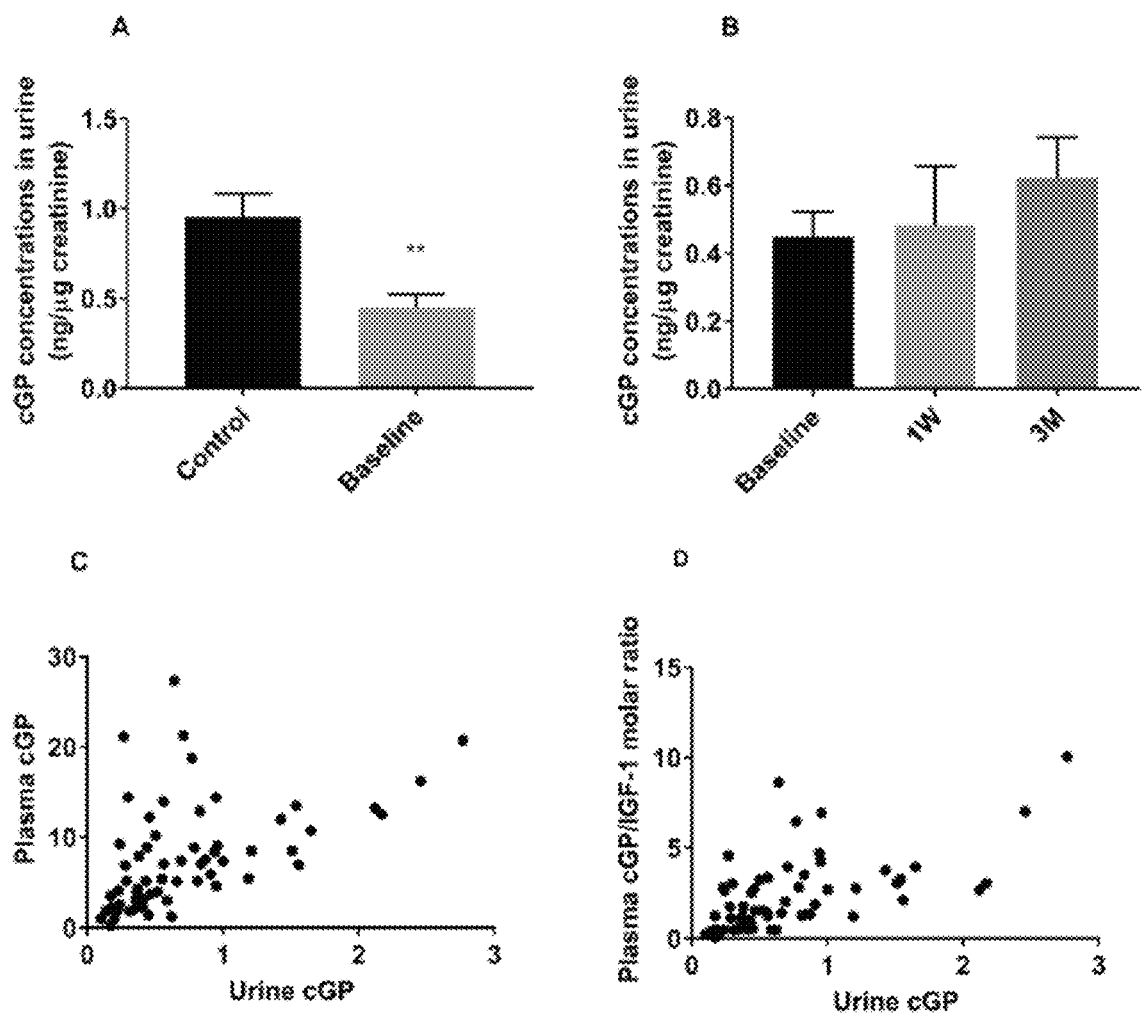
FIG. 8 shows the data collected from a urine analysis. The difference of cGP in urine between the age matched controls and stroke is similar to that observed for plasma samples (FIG. 8A). There was a trend toward increase of urine cGP in the later time points compared to the baseline as expected and the differences between the urine and plasma time point measurements were also not significant (FIG. 8B). The cGP concentration in urine had a significant correlation with plasma cGP concentration ($r=0.59$, $p<0.01$, FIG. 5C) and cGP/IGF-1 ratio ($r=0.63$, $p<0.001$, FIG. 8D)

FIG. 8A and FIG. 8B show the data collected from the urine analysis. The plasma cGP is significantly lower in stroke patients at the baseline (<48 h after stroke, p<0.01, n=9, FIG. 8A) than the normal controls (n=30). The difference of cGP in urine between the age matched controls and stroke is similar to that observed for plasma samples (FIG. 8A). There was a trend toward increase of urine cGP in the later time points compared to the baseline as expected and the differences between the urine and plasma time point measurements were also not significant (FIG. 5B).

Figure 9:
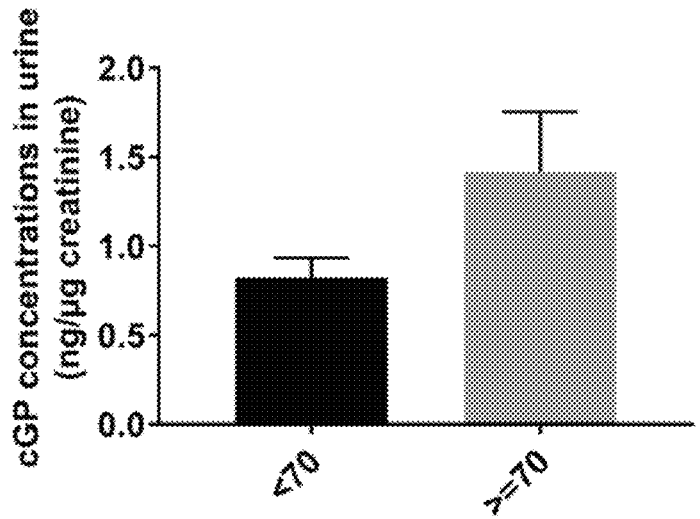
FIG. 9 shows observed changes of urine cGP in aged people. The cGP concentration in urine is significantly increased in order of old people.

The cGP concentration in urine had a significant correlation with plasma cGP concentration (r=0.59, p<0.01, FIG. 5C) and cGP/IGF-1 ratio (r=0.63, p<0.001, FIG. 8D). Similar results were observed in the urine samples between aged people and younger people (FIG. 9). The results show that urine may be used as a biological specimen as well as plasma.

Figure 10:
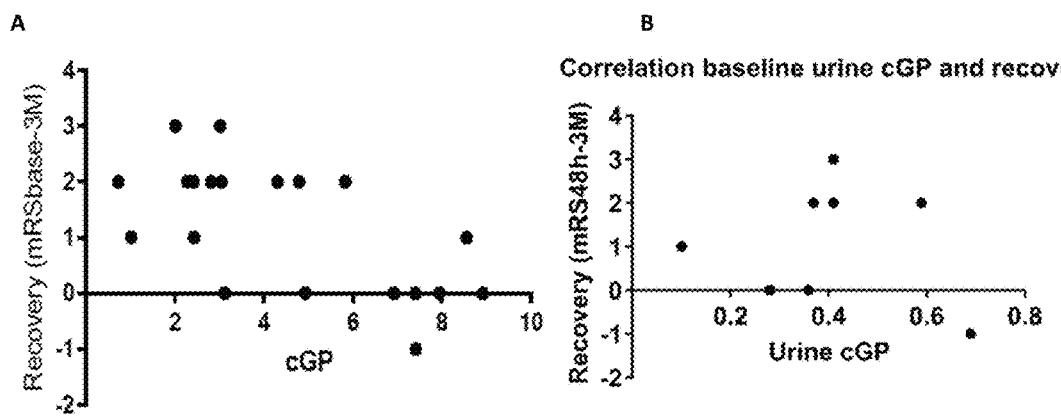
FIG. 10 shows the changes of baseline c-GP in plasma (FIG. 10A), but not urine (FIG. 10B), was associated with recovery (ΔmRS: mRS base-3M) ($r=-0.630$, $p=0.003$, FIG. 10)

FIG. 10A and FIG. 10B show the changes of baseline cGP in plasma (FIG. 10A), but not urine (FIG. 10B), was associated with recovery ($\Delta$mRS: mRS base-3M) (r=−0.630, p=0.003, FIG. 10A, 10B).

Hence the changes of cGP in urine can represent the changes of cGP in plasma.

Example 5

Art suggests that from various genotypes of blackcurrant, the anthocyanin content may be 80-700 mg per 100 ml of blackcurrant juice. It is understood that New Zealand grown blackcurrant has superior levels of anthocyanins and the Ben varieties have potentially greater concentrations of selected potentially bioactive anthocyanins. A trial was completed comparing two Ben varieties of blackcurrant against a further NZ grown variety Blackadder to confirm the presence of quantities of selected anthocyanins in the blackcurrant juice prior to any extraction and concentration.

Table 3 below shows the results.

TABLE 3

Measured Anthocyanin in Ben Varieties of Blackcurrant

| Variety | Total Anthocyanins (mg/100 ml) | Delphinidin-3-Glucoside | Delphinidin-3-Rutinoside | Cyanidin-3-Glucoside | Cyanidin-3-Rutinoside | Petunidin-3-Rutinoside | Vitamin C |
|---|---|---|---|---|---|---|---|
| Ben Ard | 597.0 | 63.1 | 221.5 | 41.2 | 248.4 | 14.4 | 246.6 |
| Ben Ard | 672.2 | 62.9 | 261.1 | 42.3 | 277.5 | 17.2 | 239.5 |
| Ben Rua | 497.0 | 28.2 | 257.4 | 0.0 | 194.0 | 11.8 | 376.8 |
| Ben Rua | 577.2 | 33.0 | 286.8 | 0.0 | 233.1 | 16.1 | 315.3 |
| Blackadder | 454.1 | 46.8 | 167.3 | 25.8 | 199.9 | 8.9 | 297.7 |
| Blackadder | 555.3 | 62.2 | 198.5 | 37.8 | 252.0 | 2.3 | 270.3 |

As can be seen above, the Ben varieties have a high total anthocyanin contents and anthocyanin profiles that vary even to other NZ grown varieties like Blackadder. The total levels measured above for all three NZ varieties are well above that noted in the art supporting the view the NZ grown blackcurrants differ to that grown elsewhere. Further it should be noted that by mixing for example the noted Ben varieties above blends of anthocyanins may be possible that differ in profile considerably to even non-Ben NZ grown varieties like Blackadder noted above.

Example 6

Figure 11:
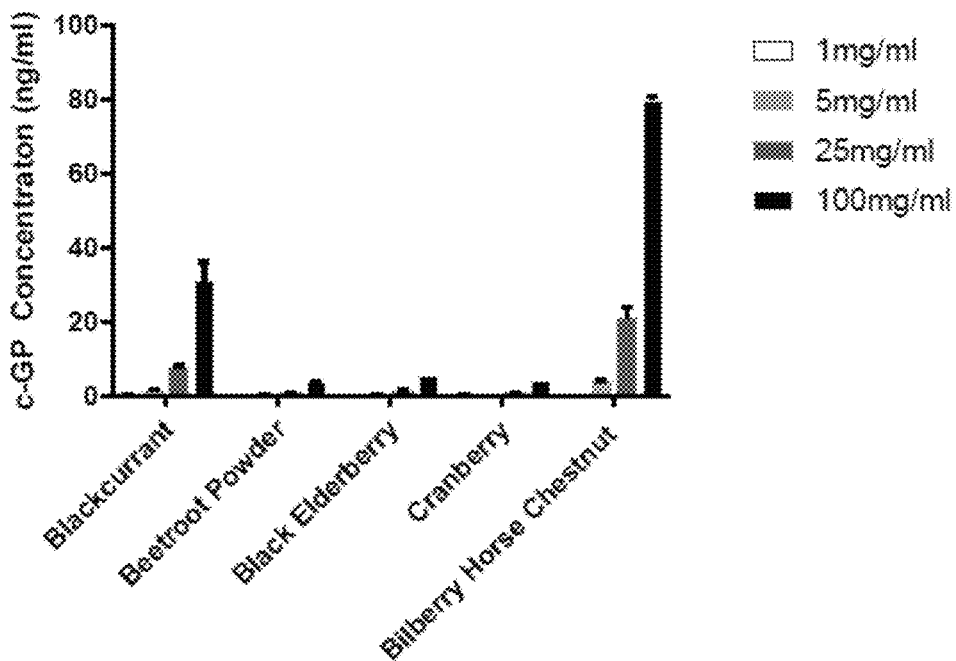
FIG. 11 shows the results of c-GP concentration content in berry fruit selected from blackcurrant, cranberry, beetroot, black elderberry and BHC complex (bilberry and horse chestnuts) in four different concentrations (1, 5, 25 and 100 mg/water)

The results from the analysis of a selection of berry fruits (blackcurrant, cranberry, beetroot, black elderberry and BHC complex (bilberry+horse chestnuts)) in four different concentrations (1, 5, 25 and 100 mg/water) containing a concentration of cGP are shown in FIG. 11.

The results indicate a concentration of cGP in blackcurrant of 30 ng/mg, which is higher than a previous blackcurrant sample supplied from Vitality. This may be due to variability in processing methods and requires further investigation. It has been noted by the inventors that this BCA sample was processed through a chromatographic column utilising a Diaion HP 20 coated resin bead which has a cGP concentration that is three times higher than a previous BCA sample extracted using a solvent extraction process.

The cGP concentration of BHC complex is 80 ng/mg and there is a fraction of cGP in black elderberry and cranberry, which may require further testing at a higher concentration.

It also has been noted that apart from blackcurrant and beetroot, the other three samples were not completely dissolved in the concentration of 100 mg.

Figure 12:
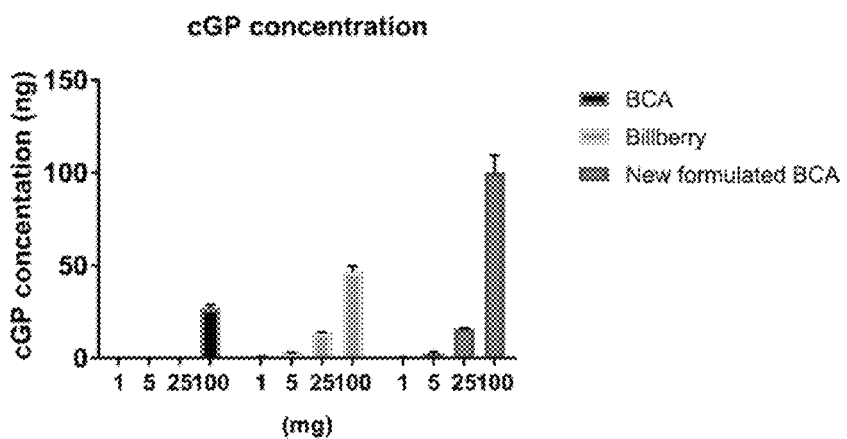
FIG. 12 shows the data from berry fruit samples as additional analysis of cGP concentration in the dose range with BCA as positive controls. The cGP concentration is 27 ng in 100 mg BCA (the control), 46.7 in 100 mg bilberry and 100 ng in 100 mg (10 ng/mg) newly formulated BCA.

FIG. 12 shows the data from the samples supplied as additional analysis in the dose range with BCA as positive controls. The cGP concentration is 27 ng in 100 mg BCA (the control), 46.7 ng in 100 mg Bilberry and 100 ng in 100 mg (10 ng/mg) newly formulated BCA.

These results again suggest that BCA processed through a chromatographic column has a higher concentration of cGP compared to BCA extracted using only an ethanol solvent extraction process. Also, bilberry alone has a lower cCP concentration than the complex of bilberry and horse chestnuts.

Figure 13:
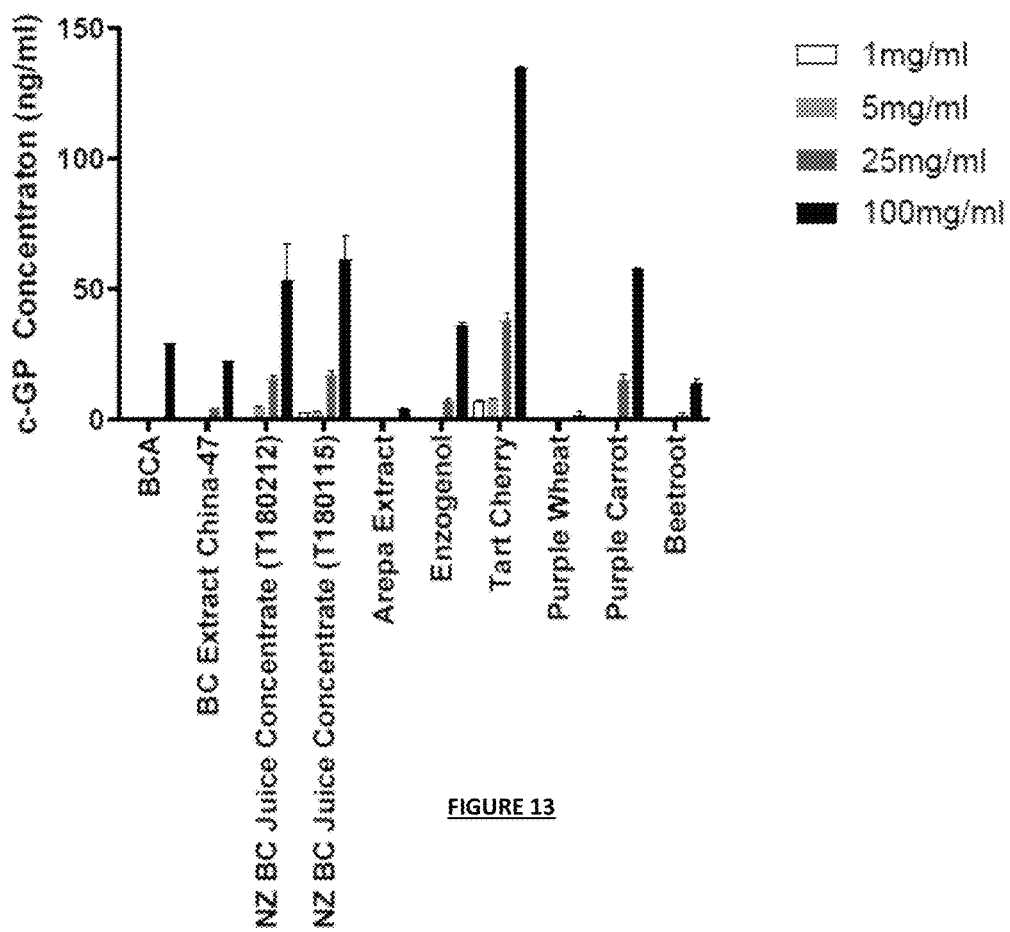
FIG. 13 shows the results from a further analysis of product samples provided by Vitality to measure cGP concentration of same. The results from the analysis of the product samples provided by Vitality (labeled as: BC extract China-47, NZBC juice concentration (T180212 and T180115), Arepa extract, Enzogenol, Tart cherry, Purple wheat, purple carrot and Beetroot) in four different concentrations (1, 5, 25 and 100 mg/water). The original Vitality BCA sample tested above with 30 ng/mg was used as positive control.

FIG. 13 shows the results from a further analysis of product samples provided by Vitality to measure cGP concentration of same. The results from the analysis of the product samples provided by Vitality (labeled as: BC extract China-47, NZBC juice concentration (T180212 and T180115), Arepa extract, Enzogenol, Tart cherry, Purple wheat, purple carrot and Beetroot) in four different concentrations (1, 5, 25 and 100 mg/water). The original Vitality BCA sample tested above with 30 ng/mg was used as positive control.

The results indicate:
Blackcurrant used as the positive control for the assays. The concentration of cGP is 29 ng/mg, which is consistent with the concentration from the analysis above, which was 30 ng/mg.
The cGP concentrations of the products are:
Tart Cherry has the highest concentration of cGP (135 ng/mg) and is 4 times greater than the Vitality BCA extract used as a positive control;
NZBC juice concentration (212) is 53 ng/mg;
NZBC juice concentration (115) is 61 ng/mg;
Purple carrot contains 57 ng/mg;
Enzogenol has similar concentration of cGP (36 ng/mg) to the Vitality BCA;
BC extract China-47 is 22 ng/mg;
Beetroot contains half the amount of cGP (14 ng/mg) compared to the Vitality BCA;
Arepa Extract has very low cGP (4 ng/mg); and
Purple wheat does not appear to contain cGP in this analysis.

It should be noted that the product samples above may contain an increased concentration of cGP from the results shown above and also purple wheat may contain cGP (although not shown in these results). As aforementioned, the cGP concentration (or presence thereof) extracted from the organic matter may be due to variability in processing methods and requires further investigation. For example, it has been noted by the inventors that organic matter initially processed through a chromatographic column utilising a Diaion HP 20 resin bead has a cGP concentration that is three times higher than a previous BCA sample extracted using an ethanol solvent extraction process alone. However, it should be appreciated that other resin beads may be utilised with similar cGP extraction capability. Furthermore, the cGP concentration extraction process may be dependent on other factors such as whether the organic matter can be dissolved in water during the assays and whether the fractions containing cGP have been correctly captured and identified in the chromatography column.

Example 7

In this Example, a study describes the good evolution of a 6-year-old girl genetically diagnosed with Rett syndrome (RTT), after having been treated with IGF-1, Melatonin (MT), blackcurrant extracts (BCA), and rehabilitation during 6 months. The patient stopped her normal development from the first year of age.

The patient showed low weight and height and met the main criteria for typical RTT. Curiously, there was pubic hair (Tanner II), very high plasma testosterone, despite low gonadotropins. No adrenal enzymatic deficits existed, and ultrasound abdominal studies were normal.

Treatment consisted in IGF-1 (0.04 mg/kg/day, 5/week, sc) during 3-months and then 15-days resting, MT (50 mg/day, orally, uninterruptedly) and neurorehabilitation.

The new blood tests were absolutely normal and the pubic hair disappeared. Then, a new treatment with IGF-1, MT, and BCA started for another 3 months. After it, pubic Tanner stage increased to III, without a known cause.

The treatment followed led to clear improvements in most of the initial impairments as shown in Tables 4 and 5.

TABLE 4

Thomas Stonell and Greenberg scale. Upon admission the patient presented a moderate drooling (score 3: wet lips and chin). This score was reduced until 1 at discharge (the patient never drools).

| Admission | Discharge |
|---|---|
| 3 | 1 |

TABLE 5

Scores reached in the Battelle Developmental inventory Screening Test (BDIST) at admission (PRE-) and at discharge (POST-). Mainly note the changes observed in adaptive behaviour, receptive communication and cognition

| Area | PRE- | POST- |
|---|---|---|
| Social/Personnel | 0 | 2 |
| Adaptive | 1 | 3 |
| Gross motor | 6 | 8 |
| Fine motor | 0 | 2 |
| TOTAL MOTOR | 3 | 6 |
| Receptive communication | 1 | 5 |
| Expressive communication | 1 | 2 |
| TOTAL COMMUNICATION | 1 | 3 |
| Cognition | 1 | 4 |
| TOTAL | 2 | 3 |

The above results support the effect of treatments with IGF-I, the antioxidant effects of MT and BC, and the increase in cyclic-glycine-proline (cGP) after BCA administration are useful for improving the neurologic disabilities existing in girls with Rett syndrome. For example, a significant finding is that Bruxism disappeared as a result of treatment. Since extracts of blackcurrant increase the levels of cGP, the mitogenic potential of IGF-1 can be counteracted, so that treatments with this hormone can be prolonged longer.

A continuous treatment with IGF-1, MT and BC may recover most of the neurologic disabilities that occur in RU with ongoing studies.

The results also indicate that the improvement of Rett syndrome after the combination treatment with cGP (additional to IGF-1 and MT), that cGP may be used for with other combinations of substances/hormones for treatment of other diseases/syndromes.

Example 8

In this Example, a further updated study to Example 3 was completed to assess plasma concentrations of cyclic glycine-proline (cGP) within 3 days after a stroke and how plasma cGP may predict short-term stroke recovery.

Stroke patients recover in function. This self-recovery process is associated with promoting the function of insulin-like growth factor-1 (IGF-1). A biomarker that represents IGF-1 function may assist to predict recovery and guide clinical management in stroke patients. Plasma IGF-1 is not all bioavailable. IGF binding protein (IGFBP)-3 and cyclic glycine-proline (cGP) collectively regulates the bioavailability of IGF-1. Plasma IGF-1, IGFBP-3 and cGP concentrations were evaluated as a biomarker for IGF-1 function and their associations with clinical outcome and recovery in stroke patients.

Methods

Fifty age-matched control subjects (women/men 35/15) and 34 people with stroke (women/men 15/19) were recruited within 3 days of stroke. Clinical assessments included the National Institutes of Health Stroke Scale (NIHSS) at baseline (<3 days), then day 7 and 90, and the modified Rankin Scale (mRS) and Fugl-Meyer Upper Limb Assessment Scale (FM) at day 7 and 90.

Plasma samples were collected from 34 stroke patients at the baseline, from 21 patients at day 7 and from 26 patients at day 90.

28 patients had completed follow ups. Amongst them 21 patients provided plasma samples at day 7 and 26 patients provided plasma samples at day 90. Thus, a total of 21 patients had completed clinical scores and provided plasma samples at all time intervals. 28 patients provided plasma samples at baseline and had clinical assessments at day 90. Fifty age-matched control participants (35 women) with no history of stroke were also recruited and all provided plasma samples (Tables 6 and 7):

TABLE 6

Baseline characteristics of acute stroke patients and controls

| | Control | Patients | p Value |
|---|---|---|---|
| Number of participants | 50 | 34 | |
| Age, y (mean ± SD) | 64.8 ± 10.03 | 66.79 ± 14.64 | 0.49[a] |
| F/M | 35/15 | 15/19 | 0.018[b] |
| Diabetes (%) | 2 (4) | 6 (17.6) | 0.057[c] |
| Smoker (%) | 1 (2) | 4 (11.8) | 0.153[c] |
| Ex-smoker (%) | 16 (32) | 9 (26.5) | 0.586[c] |
| Hypertension (%) | 13 (26) | 15 (44.1) | 0.084[b] |
| Dyslipidaemia (%) | 9 (18) | 12 (35.3) | 0.072[b] |
| Atrial fibrillation (%) | 4 (8) | 9 (26.5) | 0.022[b] |

[a]t-test;
[b]Chi-Square tests;
[c]Fisher's exact test;

TABLE 7

Correlation between biological changes at <3 days and clinical outcome and recovery of 90 days

| | | IGF-1 | IGFBP-3 | cGP | cGP/IGF-1 ratio |
|---|---|---|---|---|---|
| NIHSS | B | .006 | .000 | −.069 | −.309 |
| (n = 28) | p | .112 | .096 | .365 | .032* |
| mRS | B | −.001 | .000 | .093 | .198 |
| (n = 28) | p | .723 | .525 | .109 | .089 |
| FM | B | −.016 | −.002 | .841 | 2.331 |

TABLE 7-continued

Correlation between biological changes at <3
days and clinical outcome and recovery of 90 days

|  |  | IGF-1 | IGFBP-3 | cGP | cGP/IGF-1 ratio |
|---|---|---|---|---|---|
| (n = 27) | p | .642 | .384 | .169 | .057 |
| ΔNIHSS | B | −.006 | .000 | .069 | .309 |
| (n = 28) | p | .112 | .096 | .365 | .032* |

NIHSS, the National Institutes of Health Stroke Scale. ΔNIHSS, the change between baseline and 90 days in the National Institutes of Health Stroke Scale. mRS, the modified Rankin Scale score. FM, The Fugl- Meyer Upper Limb Assessment Scale score. The analysis was adjusted with age and baseline NIHSS.
Concentrations of IGF-1, IGFBP-3 or cGP were measured using ELISA or High-Performance Liquid Chromatography mass-spectrometry a previously described.

Results

The control participants had no significant neurological deficits (NIHSS median (range): 0 (0-2)) nor global disability (mRS median (range) 0 (0-1)) with normal up limb functions (FM median (range): 66 (65-66)). In stroke patients, the stroke severity (NIHSS) and disability (mRS) were reduced and upper limb function (FM) were improved over time. For example, NIHSS scores improved over time (F (2, 20)=27.48, p<0.001, n=21, FIG. 14A). Compared to baseline, the NIHSS score reduced by day 7 (median: 2 vs 4, p=0.01) and day 90 (median: 1 vs 4, p<0.001). The mRS score also improved from (median: 3 vs 2, p=0.003, n=21, FIG. 14) as did the FM scores (median: 64 vs 65, p=0.001, n=21, FIG. 14C).

Figure 15:
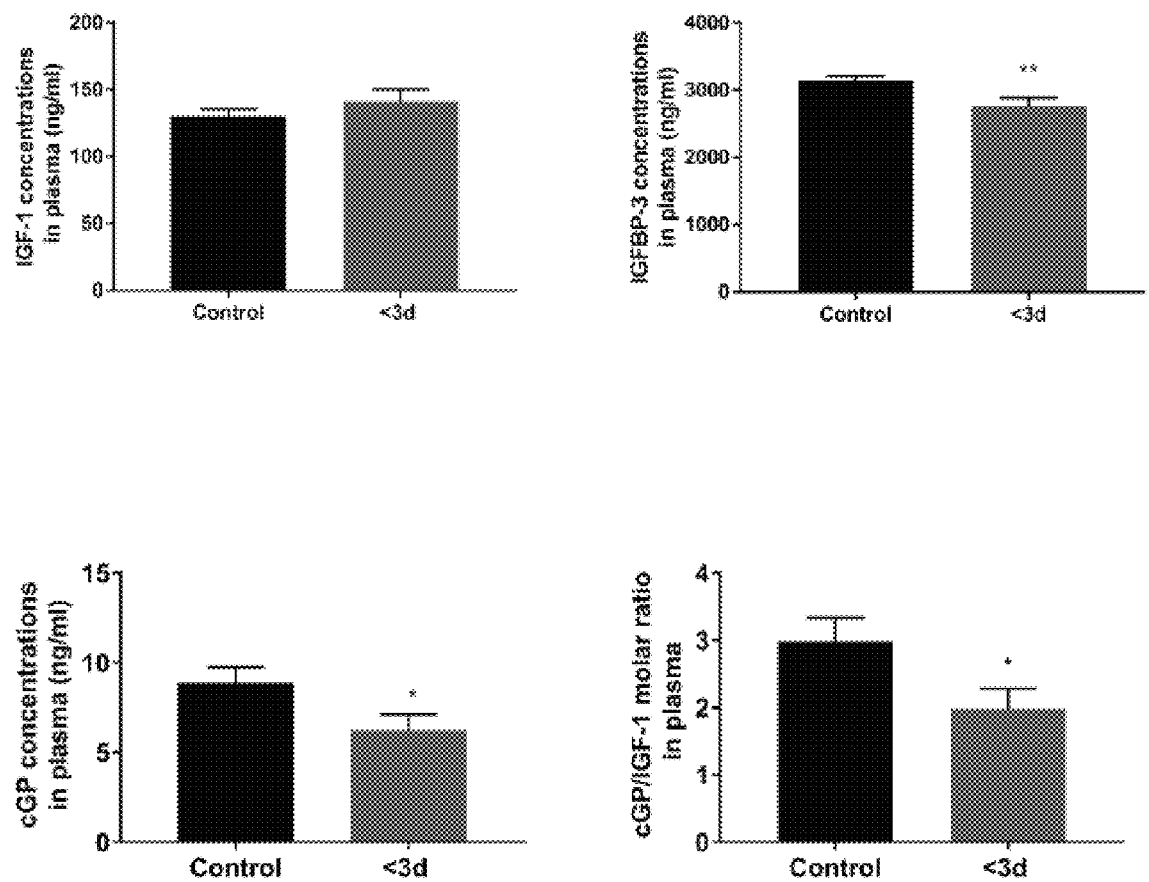
FIG. 15 illustrates graphs showing measured changes of IGF-1 (FIG. 15A), IGFBP-3 (FIG. 15B), cGP (FIG. 15C)

Baseline concentrations of IGFBP-3, cGP and cGP/IGF-1 molar ratio were lower in the stroke patients than the control subjects. In particular, compared to the control group, IGFBP-3 concentration (p=0.002, FIG. 15B), cGP concentrations (p=0.047, FIG. 15C) and cGP/IGF-1 molar ratio (p=0.043, FIG. 15D) were lower in the stroke group at baseline. There was no difference in IGF-1 concentration (FIG. 15A) between the control and stroke groups. The IGF-1/IGFBP-3 ratio at the baseline was higher in stroke group than that of control group.

Figure 16:
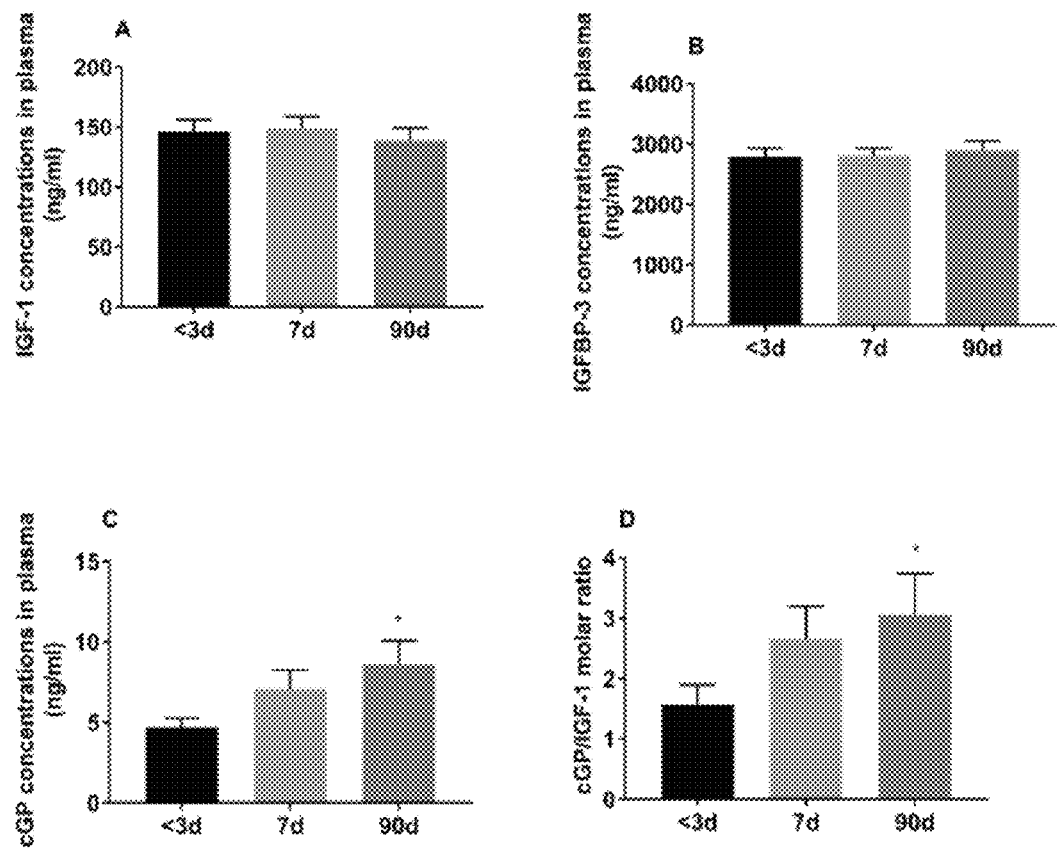
FIG. 16 illustrates graphs showing measured changes of IGF-1 (FIG. 16A), IGFBP-3 (FIG. 16B), cGP (FIG. 16C) and c-GP/IGF-1 ratio (FIG. 16D) of stroke patients <3, 7 and 90 days respectively

Plasma cGP and cGP/IGF-1 molar ratio, but not IGF-1 and IGFBP-3, increased over time. The baseline cGP/IGF-1 molar ratio was correlated with the changes in NIHSS scores from the baseline to 90 days. In particular, ANOVA repeated analysis showed the significant increases in cGP concentrations (F (2, 20)=5.345, p=0.01, n=21, FIG. 16C) and cGP/IGF-1 molar ratio (F (2, 20)=3.946, p=0.029, n=21, FIG. 16D) over time after stroke. Compared to the baseline, the concentration of cGP (p=0.014) and cGP/IGF-1 ratio (p=0.031) was significantly increased by 90 days. The concentrations of IGF-1, IGFBP-3 and IGF-1/IGFBP-3 molar ratio remained stable over time (FIGS. 16A, B).

DISCUSSION

This study has shown lower plasma concentrations of cGP, IGFBP-3 and cGP/IGF-1 ratio shortly (<3 days) after stroke onset, suggesting an impairment of autocrine regulation of IGF-1. Over the next 90 days, stroke patients showed the improvement in neurological function and global disability. This is in parallel with a gradual increase of plasma cGP and cGP/IGF-1 ratio. The patients with higher cGP/IGF-1 ratio at baseline made better recovery in neurological function 90 days after stroke. These results may suggest a role for autocrine regulation of IGF-1 in stroke recovery. The acute changes in the ratio of cGP/IGF-1 may be a potential biomarker to predict stroke recovery.

The amount of bioavailable IGF-1 in plasma is collectively regulated by IGFBP-3 and cGP. Lower IGFBP-3 and higher cGP can increase bioavailable IGF. Compared to the age-matched controls, the concentrations of IGFBP-3 and cGP were lower in stroke patients at the baseline. Hypertensive women also have shown lower plasma IGFBP-3 and cGP compared to the normotensive women suggesting an involvement in cardiovascular function. The reduction of plasma IGFBP-3 in stroke and hypertensive patients is an autocrine response to improve bioavailable IGF-1. The lower plasma cGP suggests an impairment of autocrine regulation. The conclusion is also supported by the observations that cGP administration prevents ischemic brain injury in rats and normalises the systemic blood pressure in hypertensive rats The function of cGP in vascular protection has been described both by in vivo and in vitro studies. Although it is not significant, almost half of stroke patients and only a quarter of control participants in the above study were hypertensive. Hypertension is a major risk factor of stroke and the impairment of autocrine regulation of IGF-1 may be a pathophysiology shared by hypertension and stroke.

cGP is a stable, small and lipophilic cyclic peptide with the ability to cross the blood-brain barrier (BBB). The endogenous concentrations of cGP in the cerebrospinal fluid (CSF) are approximately 50% of that in the plasma of Parkinson disease patients. The central uptake of a cGP analogue is enhanced by >100% during first 2 hours after hypoxic-ischemic brain injury in rats Thus, we could not exclude the likelihood that brain injury had promoted central uptake of cGP from plasma and thus lowered plasma cGP levels during the acute phase of stroke.

Most patients in this study made a partial recovery over time as shown by the improvement in neurological function and stroke outcome during 90-day follow ups. These clinical improvements were in parallel with an increase of cGP concentrations and cGP/IGF-1 ratio over time. The improvement of plasm IGF-1 bioavailability may contribute to the functional recovery. The baseline NIHSS and age are crucial factors that influence stroke recovery. It is essential to analyse the true relationship between biological changes and clinical outcomes with these potential confounders. The correlation analysis with the adjustment of age and baseline NIHSS scores showed that the patients with a higher molar ratio of cGP/IGF-1 at the baseline had less neurological deficits at day 90 of stroke and made a better recovery in neurological function 90 days after stroke.

Either a lower or a higher plasma IGF-1 concentration has been reported in patients 3 days after stroke compared to the control groups. The changes in plasma IGF-1 concentration only predict the mortality but not functional recovery of stroke patients. The inventor's observation from this study did not see any changes in IGF-1 concentration during the 90-day follow ups. This evidence supports the suggestion that the change in plasma concentration IGF-1 is not a reliable measure for IGF-1 function.

These promising results suggest that cGP-related change in plasma is a sensitive biomarker for IGF-1 function.

Conclusions

Low cGP concentrations and cGP/IGF-1 ratio suggest an impairment of autocrine regulation of IGF-1 in stroke. The increase of cGP concentration and cGP/IGF-1 ratio may be associated with clinical recovery at 3 months. The cGP/IGF-1 ratio at admission, if further confirmed in a larger study, may be a biomarker for predicting the recovery in stroke patients. Also, the progressive decline of cGP concentration in hypertensive patients may also be a biomarker for stroke risk.

Aspects of methods relating to the clinical application of cyclic glycine-proline (cGP) biomarker for prediction of risk and recovery of non-neurological and/or neurological conditions and the use of a concentrated extract of blackcurrant anthocyanins (BCA)/cGP containing organic or plant based materials for the treatment of same have been described by way of example only and it should be appreciated that modifications and additions may be made thereto without departing from the scope of the claims herein.

What is claimed is:

1. A method of treating a stroke or Parkinson's disease in a human in need thereof consisting essentially of:
    a) obtaining a biological specimen from the human in need thereof;
    b) measuring the concentration of cyclic glycine-proline (cGP) and/or a ratio of cGP concentration to the total measured amount of IGF-1 in the biological specimen from the human in need thereof, as a biomarker for an active, concentration-dependent IGF-1 bioavailability in the biological specimen from the human;
    c) comparing either the measured cGP concentration and/or the ratio of cGP concentration to the total measured amount of IGF-1 in the biological specimen from the human to a standard, wherein the standard is based on data collected for a cGP concentration and/or a ratio of cGP concentration to total measured amount of IGF-1 in:
        (i) the stroke or Parkinson's disease human; and/or
        (ii) a human population of stroke or Parkinson's disease human patients to confirm whether or not the human has an altered cGP concentration and/or ratio of cGP concentration to the total measured amount of IGF-1 compared to the standard;
    d) selecting the human for treatment based on the measured cGP concentration or ratio of cGP concentration to total measured amount of IGF-1 compared to the standard; and
    e) administering a therapeutically effective amount of a blackcurrant extract to the selected human for treatment, wherein the therapeutically effective amount of the blackcurrant extract is a dose of 50 mg to 1000 mg of the blackcurrant extract to the selected human per day to effectively treat the stroke or the Parkinson's disease in the selected human.

2. The method as claimed in claim 1, wherein the biological specimen is selected from the group consisting of cerebrospinal fluid, plasma, urine, and tears of the human.

3. The method as claimed in claim 1, wherein the blackcurrant extract is administered orally or by parenteral administration to the selected human.

* * * * *